United States Patent
Lucisano et al.

(10) Patent No.: US 10,660,550 B2
(45) Date of Patent: May 26, 2020

(54) IMPLANTABLE SENSOR APPARATUS AND METHODS

(71) Applicant: GLYSENS INCORPORATED, San Diego, CA (US)

(72) Inventors: Joseph Lucisano, San Diego, CA (US); Jonathan Wilensky, San Diego, CA (US); Robert Engler, Del Mar, CA (US)

(73) Assignee: GLYSENS INCORPORATED, San Diego, CA (US)

( * ) Notice: Subject to any disclaimer, the term of this patent is extended or adjusted under 35 U.S.C. 154(b) by 549 days.

(21) Appl. No.: 14/982,346

(22) Filed: Dec. 29, 2015

(65) Prior Publication Data

US 2017/0181674 A1 Jun. 29, 2017

(51) Int. Cl.
*A61B 5/00* (2006.01)
*A61B 5/145* (2006.01)
(Continued)

(52) U.S. Cl.
CPC ........ *A61B 5/14503* (2013.01); *A61B 5/0031* (2013.01); *A61B 5/14532* (2013.01);
(Continued)

(58) Field of Classification Search
CPC ....... A61B 5/145; A61B 17/3209; A61B 5/00; A61B 5/14503; A61B 5/14532;
(Continued)

(56) References Cited

U.S. PATENT DOCUMENTS 2,508,523 A 5/1950 Krebs
2,563,062 A 8/1951 Perley
(Continued)

FOREIGN PATENT DOCUMENTS

CN 1355670 A 6/2002
CN 1592570 A 3/2005
(Continued)

OTHER PUBLICATIONS

4082 & 3804 Platinum Conductors data sheet, MEMS & Sensor materials, Ferro Electronic Materials.
(Continued)

*Primary Examiner* — Eric J Messersmith
(74) *Attorney, Agent, or Firm* — Gazdzinski & Associates, PC

(57) ABSTRACT

Implantable sensor apparatus and methods of implantation. In one embodiment, a fully implantable, biocompatible sensor is disposed within a cavity or pocket formed within a living being, such that the sensor remains in a desired orientation and placement so as to enhance the performance of the sensor, and mitigate the effects of one or more factors potentially deleterious to the operation of the sensor and the host being. In one implementation, the sensor comprises an implantable biocompatible oxygen-based glucose sensor which is implanted deep within the being's torso tissue proximate the extant fascia, and oriented such that an active detector aspect of the device faces away from the being's skin surface. In one variant, the deep placement, orientation, and construction of the sensor itself cooperate to enhance the performance of the sensor, especially over extended periods of time, with little need for external calibration.

25 Claims, 11 Drawing Sheets

(51) Int. Cl.
  *A61M 5/172* (2006.01)
  *A61B 17/3209* (2006.01)
  *A61M 5/14* (2006.01)

(52) U.S. Cl.
  CPC .... *A61B 5/14542* (2013.01); *A61B 17/32093* (2013.01); *A61M 5/1723* (2013.01); *A61B 5/0004* (2013.01); *A61B 5/0015* (2013.01); *A61B 5/72* (2013.01); *A61M 5/14* (2013.01); *A61M 2210/1021* (2013.01); *A61M 2230/005* (2013.01); *A61M 2230/201* (2013.01)

(58) Field of Classification Search
  CPC .......... A61B 5/14542; A61B 17/32093; A61B 5/0031; A61B 5/72; A61B 5/0015; A61B 5/0004; A61M 5/172; A61M 5/14; A61M 5/1723; A61M 2210/1021; A61M 2230/005; A61M 2230/201
  See application file for complete search history.

(56) References Cited

U.S. PATENT DOCUMENTS

| | | |
|---|---|---|
| 2,805,191 A | 9/1957 | Hersch |
| 2,864,750 A | 12/1958 | Hughes, Jr. et al. |
| 2,998,371 A | 8/1961 | Sabins |
| 3,099,575 A | 7/1963 | Hill |
| 3,246,235 A | 4/1966 | Allsopp |
| 3,249,250 A | 5/1966 | McKee |
| 3,300,345 A | 1/1967 | Lyons, Jr. |
| 3,308,046 A | 3/1967 | Suleski |
| 3,458,421 A | 7/1969 | Dahms |
| 3,505,195 A | 4/1970 | Nielsen et al. |
| 3,542,662 A | 11/1970 | Hicks et al. |
| 3,616,412 A | 10/1971 | Gnage |
| 3,957,613 A | 5/1976 | Macur |
| 4,036,716 A | 7/1977 | Hulthe |
| 4,088,550 A | 5/1978 | Malkin |
| 4,240,438 A | 12/1980 | Shults et al. |
| 4,306,952 A | 12/1981 | Jansen |
| 4,340,457 A | 7/1982 | Kater |
| 4,361,153 A | 11/1982 | Slocum et al. |
| 4,366,033 A | 12/1982 | Richter et al. |
| 4,431,004 A | 2/1984 | Bessman et al. |
| 4,458,686 A | 7/1984 | Clark, Jr. |
| 4,484,987 A | 11/1984 | Gough |
| 4,494,950 A | 1/1985 | Fischell |
| 4,541,431 A | 9/1985 | Ibrahim et al. |
| 4,550,732 A | 11/1985 | Batty, Jr. et al. |
| 4,553,547 A | 11/1985 | Keimel |
| 4,571,589 A | 2/1986 | Slocum et al. |
| 4,637,861 A | 1/1987 | Krull et al. |
| 4,650,547 A | 3/1987 | Gough |
| 4,671,288 A | 6/1987 | Gough |
| 4,703,756 A | 11/1987 | Gough et al. |
| 4,746,218 A | 5/1988 | Lord, III |
| 4,748,562 A | 5/1988 | Miller et al. |
| 4,759,828 A | 7/1988 | Young et al. |
| 4,781,798 A | 11/1988 | Gough |
| 4,830,713 A | 5/1989 | Gagescu |
| 4,890,620 A | 1/1990 | Gough |
| 5,042,902 A | 8/1991 | Huebscher et al. |
| 5,046,242 A | 9/1991 | Kuzma |
| 5,077,476 A | 12/1991 | Rosenthal |
| 5,105,811 A | 4/1992 | Kuzma |
| 5,112,455 A | 5/1992 | Cozzette et al. |
| 5,150,516 A | 9/1992 | Boero et al. |
| 5,165,406 A | 11/1992 | Wong |
| 5,189,717 A | 2/1993 | Larson et al. |
| 5,264,103 A | 11/1993 | Yoshioka |
| 5,272,283 A | 12/1993 | Kuzma |
| 5,273,203 A | 12/1993 | Webster |
| 5,283,104 A | 2/1994 | Aoude et al. |
| 5,283,204 A | 2/1994 | Rhodes et al. |
| 5,284,140 A | 2/1994 | Allen et al. |
| 5,322,063 A | 6/1994 | Allen et al. |
| 5,337,475 A | 8/1994 | Aoude et al. |
| 5,395,504 A | 3/1995 | Saurer et al. |
| 5,431,160 A | 7/1995 | Wilkins |
| 5,487,855 A | 1/1996 | Moeggenborg et al. |
| 5,497,772 A | 3/1996 | Schulman et al. |
| 5,560,098 A | 10/1996 | Robins |
| 5,660,163 A | 8/1997 | Schulman et al. |
| 5,692,299 A | 12/1997 | Daems et al. |
| 5,695,623 A | 12/1997 | Michel et al. |
| 5,711,861 A | 1/1998 | Ward et al. |
| 5,727,283 A | 3/1998 | Webster |
| 5,741,330 A | 4/1998 | Brauker et al. |
| 5,750,926 A | 5/1998 | Schulman et al. |
| 5,776,324 A | 7/1998 | Usala |
| 5,777,060 A | 7/1998 | Van Antwerp |
| 5,782,755 A | 7/1998 | Chance et al. |
| 5,782,891 A | 7/1998 | Hassler et al. |
| 5,791,344 A | 8/1998 | Mann |
| 5,804,048 A | 9/1998 | Wong et al. |
| 5,821,011 A | 10/1998 | Taylor et al. |
| 5,842,983 A | 12/1998 | Abel et al. |
| 5,855,995 A | 1/1999 | Haq et al. |
| 5,864,088 A | 1/1999 | Sato et al. |
| 5,882,494 A | 3/1999 | Van Antwerp |
| 5,887,240 A | 3/1999 | Fournier et al. |
| 5,932,175 A | 8/1999 | Knute et al. |
| 5,942,842 A | 8/1999 | Fogle, Jr. |
| 5,964,993 A | 10/1999 | Blubaugh, Jr. et al. |
| 5,985,129 A | 11/1999 | Gough et al. |
| 6,001,067 A | 12/1999 | Shults |
| 6,027,479 A | 2/2000 | Alei et al. |
| 6,041,496 A | 3/2000 | Haq et al. |
| 6,081,736 A | 6/2000 | Colvin et al. |
| 6,090,503 A | 7/2000 | Taylor et al. |
| 6,096,066 A | 8/2000 | Chen et al. |
| 6,107,083 A | 8/2000 | Collins et al. |
| 6,119,208 A | 9/2000 | White et al. |
| 6,193,421 B1 | 2/2001 | Tamekuni et al. |
| 6,200,772 B1 | 3/2001 | Vadgama et al. |
| 6,212,416 B1 | 4/2001 | Ward et al. |
| 6,221,513 B1 | 4/2001 | Lasater |
| 6,403,944 B1 | 6/2002 | MacKenzie et al. |
| 6,466,810 B1 | 10/2002 | Ward et al. |
| 6,516,808 B2 | 2/2003 | Schulman |
| 6,551,252 B2 | 4/2003 | Sackner et al. |
| 6,558,321 B1 | 5/2003 | Burd et al. |
| 6,642,015 B2 | 11/2003 | Vachon et al. |
| 6,721,587 B2 | 4/2004 | Gough |
| 6,741,877 B1 | 5/2004 | Shults et al. |
| 6,809,607 B2 | 10/2004 | Nagasaka |
| 6,812,404 B1 | 11/2004 | Martinez |
| 6,832,114 B1 | 12/2004 | Whitehurst et al. |
| 6,843,107 B2 | 1/2005 | Newman et al. |
| 6,931,268 B1 | 8/2005 | Kiani-Azarbayjany et al. |
| 7,005,796 B2 | 2/2006 | Kolluri et al. |
| 7,079,881 B2 | 7/2006 | Schulman et al. |
| 7,106,939 B2 | 9/2006 | LaBrake et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,140,787 B2 | 11/2006 | Yamauchi et al. |
| 7,146,203 B2 | 12/2006 | Botvinick et al. |
| 7,161,727 B2 | 1/2007 | Callies et al. |
| 7,189,341 B2 | 3/2007 | Li et al. |
| 7,226,978 B2 | 6/2007 | Tapsak et al. |
| 7,248,912 B2 | 7/2007 | Gough et al. |
| 7,323,142 B2 | 1/2008 | Pendo et al. |
| 7,336,984 B2 | 2/2008 | Gough et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,988 B2 | 1/2009 | Ok et al. |
| 7,497,827 B2 | 3/2009 | Brister et al. |
| 7,514,791 B2 | 4/2009 | Shah et al. |
| 7,525,298 B2 | 4/2009 | Morgan et al. |
| 7,761,130 B2 | 7/2010 | Simpson et al. |
| 7,857,760 B2 | 12/2010 | Brister et al. |
| 7,871,456 B2 | 1/2011 | Gough et al. |

(56) References Cited

U.S. PATENT DOCUMENTS

| | | | |
|---|---|---|---|
| 7,875,293 B2 | 1/2011 | Shults et al. | |
| 7,881,763 B2 | 2/2011 | Brauker et al. | |
| 7,894,870 B1 | 2/2011 | Lucisano et al. | |
| 8,133,178 B2 | 3/2012 | Brauker | |
| 8,270,661 B2 | 9/2012 | Sorensen et al. | |
| 8,357,107 B2 | 1/2013 | Draudt et al. | |
| 8,690,820 B2 | 4/2014 | Cinar et al. | |
| 8,763,245 B1 | 7/2014 | Lucisano et al. | |
| 9,002,711 B2 | 4/2015 | Morinaka et al. | |
| 9,119,528 B2 | 9/2015 | Cobelli et al. | |
| 9,247,901 B2 | 2/2016 | Kamath et al. | |
| 9,325,060 B2 | 4/2016 | Kalistaja et al. | |
| 9,362,776 B2 | 6/2016 | Low et al. | |
| 9,444,027 B2 | 9/2016 | Dibra et al. | |
| 9,451,908 B2 | 9/2016 | Kamath et al. | |
| 2002/0026108 A1 | 2/2002 | Colvin et al. | |
| 2002/0123087 A1 | 9/2002 | Vachon et al. | |
| 2002/0156355 A1 | 10/2002 | Gough | |
| 2002/0161286 A1 | 10/2002 | Gerber et al. | |
| 2002/0193671 A1 | 12/2002 | Ciurczak | |
| 2003/0048621 A1 | 3/2003 | Blood et al. | |
| 2003/0049166 A1 | 3/2003 | Pendo | |
| 2003/0053784 A1 | 3/2003 | LaBrake et al. | |
| 2003/0126593 A1 | 7/2003 | Mault | |
| 2003/0179167 A1 | 9/2003 | Kolluri et al. | |
| 2003/0181794 A1 | 9/2003 | Rini et al. | |
| 2003/0187338 A1 | 10/2003 | Say et al. | |
| 2003/0217966 A1 | 11/2003 | Tapsak et al. | |
| 2003/0228681 A1 | 12/2003 | Ritts et al. | |
| 2004/0011671 A1 | 1/2004 | Shults et al. | |
| 2004/0012935 A1 | 1/2004 | Tagi et al. | |
| 2004/0057043 A1 | 3/2004 | Newman et al. | |
| 2004/0064133 A1 | 4/2004 | Miller et al. | |
| 2004/0106857 A1 | 6/2004 | Gough et al. | |
| 2004/0158194 A1 | 8/2004 | Wolff et al. | |
| 2004/0167080 A1 | 8/2004 | Dodge et al. | |
| 2004/0176669 A1 | 9/2004 | Colvin, Jr. | |
| 2004/0190111 A1 | 9/2004 | Callies et al. | |
| 2004/0199059 A1* | 10/2004 | Brauker | A61B 5/14532 600/309 |
| 2004/0220459 A1 | 11/2004 | Schlegel | |
| 2005/0027175 A1 | 2/2005 | Yang | |
| 2005/0031689 A1 | 2/2005 | Shults et al. | |
| 2005/0033132 A1 | 2/2005 | Shults et al. | |
| 2005/0052858 A1 | 3/2005 | Shima et al. | |
| 2005/0059871 A1 | 3/2005 | Gough | |
| 2005/0124873 A1 | 6/2005 | Shults et al. | |
| 2005/0154271 A1 | 7/2005 | Rasdal | |
| 2005/0177036 A1 | 8/2005 | Shults et al. | |
| 2005/0196322 A1 | 9/2005 | Truex et al. | |
| 2005/0245799 A1* | 11/2005 | Brauker | A61B 5/14532 600/347 |
| 2005/0245971 A1 | 11/2005 | Brockway et al. | |
| 2005/0251083 A1 | 11/2005 | Carr-Brendel | |
| 2005/0272989 A1 | 12/2005 | Shah et al. | |
| 2006/0085137 A1 | 4/2006 | Bartkowiak et al. | |
| 2006/0086624 A1 | 4/2006 | Tapsak et al. | |
| 2006/0195029 A1 | 8/2006 | Shults et al. | |
| 2006/0204536 A1 | 9/2006 | Shults et al. | |
| 2006/0257995 A1 | 11/2006 | Simpson et al. | |
| 2006/0257996 A1 | 11/2006 | Simpson et al. | |
| 2006/0263763 A1 | 11/2006 | Simpson et al. | |
| 2007/0151868 A1 | 7/2007 | Staib et al. | |
| 2008/0033269 A1 | 2/2008 | Zhang | |
| 2008/0033272 A1 | 2/2008 | Gough et al. | |
| 2008/0039702 A1 | 2/2008 | Hayter et al. | |
| 2008/0197024 A1 | 8/2008 | Simpson et al. | |
| 2008/0200791 A1 | 8/2008 | Simpson et al. | |
| 2008/0317276 A1 | 12/2008 | Sorensen et al. | |
| 2009/0281399 A1 | 11/2009 | Keel et al. | |
| 2010/0041971 A1 | 2/2010 | Goode, Jr. et al. | |
| 2010/0145317 A1 | 6/2010 | Laster et al. | |
| 2010/0149042 A1 | 6/2010 | Utsi et al. | |
| 2011/0137142 A1 | 6/2011 | Lucisano et al. | |
| 2012/0262298 A1 | 10/2012 | Bohm et al. | |
| 2012/0283960 A1 | 11/2012 | Budiman | |
| 2012/0323100 A1 | 12/2012 | Kamath et al. | |
| 2013/0016573 A1 | 1/2013 | Goel et al. | |
| 2013/0030273 A1 | 1/2013 | Tapsak et al. | |
| 2013/0172692 A1 | 7/2013 | Choi et al. | |
| 2013/0178727 A1 | 7/2013 | Hayter et al. | |
| 2013/0197332 A1 | 8/2013 | Lucisano et al. | |
| 2014/0046148 A1 | 2/2014 | Simpson | |
| 2014/0309510 A1 | 10/2014 | Lucisano et al. | |
| 2014/0323960 A1 | 10/2014 | Sloan | |
| 2014/0350652 A1* | 11/2014 | Suwito | A61N 1/0541 607/116 |
| 2015/0163602 A1 | 6/2015 | Pedersen et al. | |
| 2015/0250429 A1 | 9/2015 | Hampapuram et al. | |
| 2015/0289823 A1 | 10/2015 | Rack-Gomer et al. | |
| 2015/0335285 A1 | 11/2015 | Poon et al. | |
| 2016/0022180 A1 | 1/2016 | Joseph et al. | |
| 2016/0073964 A1 | 3/2016 | Cobelli et al. | |
| 2016/0134980 A1 | 5/2016 | Abolfathi | |
| 2016/0163174 A1 | 6/2016 | Zhang | |
| 2016/0235300 A1 | 8/2016 | Goodnow | |
| 2016/0317744 A1 | 11/2016 | Rule | |
| 2017/0173262 A1 | 6/2017 | Veltz | |
| 2017/0181628 A1 | 6/2017 | Burnette et al. | |
| 2017/0181630 A1 | 6/2017 | Mahalingam et al. | |
| 2017/0325725 A1 | 11/2017 | Shah et al. | |
| 2017/0347932 A1 | 12/2017 | Lucisano et al. | |
| 2017/0357776 A1 | 12/2017 | Baker et al. | |
| 2018/0000395 A1 | 1/2018 | Lucisano et al. | |
| 2018/0140239 A1 | 5/2018 | Lucisano et al. | |
| 2018/0153450 A1 | 6/2018 | Routh | |

FOREIGN PATENT DOCUMENTS

| | | |
|---|---|---|
| CN | 101006374 A | 7/2007 |
| CN | 201207090 Y | 3/2009 |
| EP | 0852414 B1 | 11/2004 |
| JP | H11295556 A | 10/1999 |
| JP | 2000121863 A | 4/2000 |
| JP | 2005308982 A | 11/2005 |
| JP | 2007121886 A | 5/2007 |
| WO | WO-9213271 A1 | 8/1992 |
| WO | WO-2008013881 A2 | 1/2008 |
| WO | WO-2011018407 A1 | 2/2011 |
| WO | WO-2011120014 A1 | 9/2011 |
| WO | WO-2013016573 A1 | 1/2013 |
| WO | WO-2014035672 A2 | 3/2014 |

OTHER PUBLICATIONS

Allcock H.R., et al., "Contemporary Polymer Chemistry," Pearson Education Upper Saddle River, NJ, 2003.

Alvarez-Icaza M., et al., "Mass Production of Biosensors," Analytical Chemistry, 1993, vol. 65 (11), pp. 525-533.

Andrade J.D., Surface and Interfacial Aspects of Biomedical Polymers: vol. 1 Surface Chemistry and Physics, 1985.

Armour J.C., et al., "Application of a Chronic intravascular Blood Glucose Sensor in Dogs," Diabetes, 1990, vol. 39 (12), pp. 1519-1526.

Bard A.J., et al., "Electrochemical Methods: Fundamentals and Applications," 2nd Edition, 2000.

Bilitewski U., et al., "Glucose Biosensors Based on Thick Film Technology," Biosensors & Bioelectronics, 1991, vol. 6, pp. 369-373.

Billmeyer F., Textbook of Polymer Science, 3rd Edition, John Wiley, 1984.

Bremer T.M., et al., "Benchmark Data from the Literature for Evaluation of New Glucose Sensing Technologies," Diabetes Technology & therapeutics, 2001, vol. 3 (3), pp. 409-418.

Cermet Platinum Conductor data sheet, 5542 Print GD, 5542 Pouring GD, Electro-Science Laboratories,Inc.

Cha, C.S., et al., "Electrochemical Behaviour of Microfabricated Thick-film Electrodes," Sensors and Actuators B., 1990, vol. 2, pp. 277-281.

Choleau, et al., "Calibration of a Subcutaneous Amperometric Glucose Sensor Implanted for 7 Days in Diabetic Patients Part 2.

(56) References Cited

OTHER PUBLICATIONS

Superiority of the One-point Calibration Method," Biosensors and Bioelectronics, 2002, vol. 17, pp. 641-646.
Choleau, et al., "Calibration of a Subcutaneous Amperometric Glucose Sensor Part 1. Effect of Measurement Uncertainties on the Determination of Sensor Sensitivity and Background Current.," Biosensors and Bioelectronics, 2002, vol. 17, pp. 647-654.
Conway M.J., et al., "Radio Telemetry of Blood Po2 in Vivo," Biomedical Engineering, 1973, vol. 8 (10), pp. 428-430.
Dutronc, P., et al., "Influence of the Nature of the Screen-printed Electrode Metal on the Transport and Detection Properties of Thick-film Semiconductor Gas Sensors," Sensors and Actuators B, 1992, vol. 6, pp. 279-284.
Fischer U., et al., "A Membrane Combination for Implantable Glucose Sensors. Measurements in Undiluted Biological Fluids," Transactions—American Society for Artificial Internal Organs, 1982, vol. 28, pp. 245-248.
Golonka L.J., et al., "The influence of the Electrode Material on the Sensitivity of an $Sno_2$ Thick-film Gas Sensor," Sensors and Actuators B, 1994, vol. 18-19, pp. 453-456.
Gough D.A., et al., "A Novel Rotated Disc Electrode and Time Lag Method for Characterizing Mass Transport in Liquid-membrane Systems," Journal of the American Institute of Chemical Engineers, 1980, vol. 26, pp. 1013.
Gough D.A., et al., "Membrane-covered, Rotated Disc Electrode," Analytical Chemistry, 1979, vol. 51, pp. 439-444.
Gough D.A., et al., "Two-Dimensional Enzyme Electrode Sensor for Glucose," Analytical Chemistry, 1985, vol. 57 (12), pp. 2351-2357.
Holc J., et al., "Interaction Between Thick-film Platinum Electrodes and Yttria-stabilized $Zro_2$ Ceramic," Journal of Materials Science Letters, 1989, vol. 8, pp. 635-637.
Holmes, P.J. and R.G. Loasby. Handbook of Thick Film Technology. Electrochemical Publications Ltd (Glasgow: Bell and Bain Ltd., 1976).
Jablecki M., et al., "Simulations of the Frequency Response of Implantable Glucose Sensors," Analytical Chemistry, 2000, vol. 72 (8), pp. 1853-1859.
Kovatchev B.P., et al., "Graphical and Numerical Evaluation of Continuous Glucose Sensing Time Lag," Diabetes Technology & Therapeutics, 2009, vol. 11(3), pp. 139-143.
Kroschwitz J., "Concise encyclopedia of polymer science and engineering," John Wiley, 1990.
Leypoldt J.K., et al., "Diffusion and the Limiting Substrate in Two-substrate Immobilized Enzyme Systems," Biotechnology and Bioengineering, 1982, vol. 24 (12), pp. 2705-2719.
Leypoldt J.K., et al., "Model of a Two-substrate Enzyme Electrode for Glucose," Analytical Chemistry, 1984, vol. 56 (14), pp. 2896-2904.
Lucisano, et al., "In Vitro Stability of an Oxygen Sensor," Analytical Chemistry, 1987, vol. 59 (5), pp. 736-739.
Lucisano, Ph.D. Dissertation, Univ. of Calif. (San Diego), pp. xv-xvi, 8-10, 26-30, 34-36, 96-97 (made available to the public on Dec. 15, 1988)—Call No. "T3.6.L821987".

Makale M.T., et al., "Tissue Window Chamber System for Validation of Implanted Oxygen Sensors," American Journal of Physiology. Heart and Circulatory Physiology, 2003, vol. 284 (6), pp. 2288-2294.
McKean BD., et al., "A Telemetry-Instrumentation System for Chronically Implanted Glucose and Oxygen Sensors," Biomedical Engineering, IEEE Transactions On, 1988, vol. 35 (7), pp. 526-532.
McNaught A.D., et al., "The Compendium of Chemical Terminology," The Gold Book, Second Edition, 1997.
Platinum Oxygen Sensor Materials data sheet, Component Metallizations/0S1/0S2/0S3, Heraeus.
Rich A., "Shielding and Guarding," Analog Dialogue, 1983, vol. 17 (1), pp. 8-13.
Sargent B.J., et al., "Design and Validation of the Transparent Oxygen Sensor Array," Biomedical Engineering, IEEE Transactions On, 1991, vol. 38 (5), pp. 476-482.
Anderson J.M., "Biological Responses to Materials." Annual Review of Materials Research, 2001, vol. 31, pp. 81-110.
Ma, et al., "A Biocompatible and Biodegradable Protein Hydrogel with Green and Red Autofluorescence: Preparation, Characterization and In Vivo Biodegradation Tracking and Modeling," Scientific Reports (Nature.com) published Jan. 27, 2016.
Dhakar L., "Skin Based Flexible Triboelectric Nanogenerators with Motion Sensing Capability," Micro Electro Mechanical Systems (MEMS), 2015 28th IEEE International Conference on, 2015, IEEE, pp. 106-109.
Lemey S., et al., "Wearable Flexible Lightweight Modular RFID Tag With Integrated Energy Harvester," IEEE Transactions on Microwave Theory and Techniques, 2016, vol. 64.7, pp. 2304-2314.
Takei K., et al., "Design for a 400-MHz Passive RFID Prototype System for Long Range Applications," to be published in Proc. IEEE Int. Symp. Antennas Propag. 2007.
Wong CM., et al., "Glucose Oxidase: Natural Occurrence, Function, Properties and Industrial Applications," Applied Microbiology and Biotechnology, 2008, vol. 78 (6), pp. 927-938.
ELISA Kit Manual Human C3a #550499.
ELISA Kit Manual Human C4a #5550947.
Gough, et al., "Function of an Implanted Tissue Glucose Sensor for More than 1 Year in Animals", Science Translational Medicine, Jul. 28, 2010, vol. 2 (42), pp. 42ra53.
Schultz J.S., et al., "Optical Fiber Affinity Sensors," Methods in Enzymology, K. Mosbach, Ed., Academic Press,1988, vol. 137, pp. 349-366.
West, Electrodeposition and Corrosion Processes, 1971.
Heraeus Technical Data Sheet,Thick Film Materials, Product CL11-5349, retrieved from the Internet on Jun. 14, 2019.
Heraeus Technical Data Sheet,Thick Film Materials, Product CL11-5100, retrieved from the Internet on Jun. 14, 2019.
Heraeus Technical Data Sheet,Thick Film Materials, Product CL11-6109, retrieved from the Internet on Jun. 14, 2019.
Heraeus Technical Data Sheet,Thick Film Materials, Product LP11-4493, retrieved from the Internet on Jun. 14, 2019.
Morris C.G., Definition of "Machine Learning", Academic Press Dictionary of Science and Technology (4th ed.), 1992, Oxford, UK: Elsevier Science & Technology. Retrieved from https://search.credoreference.com/content/entry/apdst/machine_learning/0?institutionId=743.

* cited by examiner

IMPLANTABLE SENSOR APPARATUS AND METHODS

GRANT INFORMATION

This invention was made in part with government support under NIH Grant No. DK-77254. The United States government has certain rights in this invention.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

1. TECHNICAL FIELD

The disclosure relates generally to the field of sensors, therapy devices, implants, and other devices which can be used consistent with human beings or other living entities, and in one exemplary aspect to methods and apparatus enabling implantation of such sensors and/or electronic devices for, e.g., monitoring of one or more physiological parameters.

2. DESCRIPTION OF RELATED TECHNOLOGY

Implantable electronics is a rapidly expanding discipline within the medical arts. Owing in part to great advances in electronics and wireless technology integration, miniaturization, and performance, sensors or other types of electronics or implantable devices (e.g., therapy agent delivery devices or materials, implants, and the like) which once were beyond the realm of reasonable use in vivo on a living subject can now be surgically implanted within such subjects with minimal effect on the recipient subject, and in fact many inherent benefits.

One particular area of note relates to blood glucose monitoring for subjects, including those with so-called "type 1" or "type 2" diabetes. As is well known, regulation of blood glucose is impaired in people with diabetes by: (1) the inability of the pancreas to adequately produce the glucose-regulating hormone insulin; (2) the insensitivity of various tissues that use insulin to take up glucose; or (3) a combination of both of these phenomena. To correct this disregulation requires blood glucose monitoring.

Currently, glucose monitoring in the diabetic population is based largely on collecting blood by "fingersticking" and determining its glucose concentration by conventional assay. This procedure has several disadvantages, including: (1) the discomfort associated with fingersticking, which should be performed repeatedly each day; (2) the near impossibility of sufficiently frequent sampling (some blood glucose excursions require sampling every 20 minutes, or more frequently, to accurately treat); and (3) the requirement that the user initiate blood collection, which precludes warning strategies that rely on automatic early detection. Using the extant fingersticking procedure, the frequent sampling regimen that would be most medically beneficial cannot be realistically expected of even the most committed patients, and automatic sampling, which would be especially useful during periods of sleep, is not available.

Implantable glucose sensors have long been considered as an alternative to intermittent monitoring of blood glucose levels by the fingerstick method of sample collection. These devices may be partially implanted, where certain components reside within the body but are physically connected to additional components external to the body via one or more percutaneous elements. Partially implanted sensors (discussed in greater detail below) are not viable for long-term use, particularly due to the undesirability of having an essentially open wound on the body for an extended period, and all of the attendant problems associated therewith (including greater risk of infection, the body's natural response to attempt to expel the percutaneous or "through the skin" portion of the implant, etc.).

Implantable sensor devices may alternatively be fully implanted, where all components of the system reside within the body, and there are no percutaneous elements. The operability of one such fully implanted sensor has been demonstrated as a central venous implant in dogs (Armour et al., Diabetes, 39:1519 1526 (1990), incorporated herein by reference in its entirety). Although this sensor provided recording of blood glucose, which is most advantageous for clinical applications, the described implantation at a central venous site poses several risks and drawbacks, including risk of blood clot formation and vascular wall damage. An alternative that does not present such risks to the user is to implant the sensor in a "solid" tissue site and to relate the resulting signal to blood glucose concentration.

Typical sensors implanted in solid tissue sites measure the concentration of solutes, such as glucose, in the blood perfusing the microcirculation in the vicinity of the sensor. Glucose diffuses from nearby capillaries to the sensor surface. Because such diffusion occurs effectively only over very small distances, the sensor responds to the substrate supply only from nearby blood vessels. Conversely, solutes that are generated in the locality of the sensor may be transported away from the sensor's immediate vicinity by the local microvasculature. In either case, the local microcirculation may influence the sensor's response.

One problem that has confronted previous attempts to implant sensors in solid tissue is that the pattern of blood vessels in the vicinity of the sensor may be highly variable, and may change with time in response to the implantation procedure and the presence of an implant. In some cases, microscopic blood vessels may be close to the sensing element, resulting in substantial diffusive flux and clear, strong signals. In other cases, blood vessels are more distant and sensors may appear not to function, to function weakly, or to function only with substantial delays.

Further complicating the spatial inhomogeneity of the microvasculature are the phenomena of vasomotion and variations in regional blood flow. Vasomotion describes the unsynchronized stop-start blood flow cycles that are observed in individual capillaries in living tissue. This phenomenon is characterized by spatial asynchrony—some capillaries have flow while immediate neighbors do not. Vasomotion does not occur continuously or frequently and may be most common when the tissue is otherwise at rest. But, when it occurs, the frequency often can be on the order of 2 to 4 cycles per minute, with flow interruption in individual capillaries ranging from partial to complete.

Regional blood flow is also affected by posture and the position of the body, such-that localized surface pressure on a blood vessel may occlude it completely, albeit temporarily. The occurrence of such complete occlusion is not predictable.

Traditionally, such "solid tissue" sensors (including the aforementioned glucose sensors) are implanted within the living subject at a generally superficial layer or level of the tissue e.g., at a prescribed superficial depth below the skin; see, e.g., Gough et al., Science Translational Medicine, 28 Jul. 2010: Vol. 2, Issue 42, pp. 42ra53, wherein individual sensor telemetry units were implanted in subcutaneous tissue sites in 20-kg anesthetized Yucatan minipigs by making an incision 5 cm long and 0.5 to 1 cm deep, retracting the skin, and exposing the dermal layers. A pocket was created between the subdermal fat and underlying muscle with blunt dissection. The implants were placed in this pocket with the sensor surface facing inward away from the skin. The foregoing superficial implantation technique is used to ostensibly (i) mitigate tissue trauma resulting from the surgical implantation procedure, and (ii) mitigate interference from interposed solid tissue to the propagation of electromagnetic radiation (e.g., wireless transmissions to and from the implant). Specifically, historically larger implants require a larger volume within the solid tissue of the recipient, and hence placing the larger implant further down into the layers of tissue, etc. residing below the epidermis requires a larger incision, possibly including through various blood vessels and other features which may extend the host's surgical recovery time, and possibly requiring removal of some solid tissue to accommodate the volume of the implant.

Moreover, the extraction or "explant" process (i.e., removal of the sensor after expiration of its useful lifetime, or for other reasons) can become more difficult and traumatic to the tissue the deeper the implant is located; such trauma is especially exacerbated if there is a significant foreign body response (FBR) which may cause tissue to responsively grow around the implant over time (e.g., fibrous encapsulation or similar processes), due to inter alia, the presence of certain compounds such as peroxides or electrical potential/current generated by the sensor. In effect, the size of the implanted device combined with the encapsulating tissue (which may be of a more fibrous and less resilient nature than the neighboring undisturbed tissue) increases over time, thereby making explant that much more difficult and traumatic to the host. In fact, many prior art fully implantable sensors actually encourage FBR to, inter alia, attempt to enhance tissue and blood vessel contact with the implanted sensor's sensing element (e.g., membrane), thereby further exacerbating difficulties with the subsequent explant, and potentially causing deleterious changes in sensor performance due to the changing relationship between the patient's tissue and the sensor.

However, restriction of the implantation of such sensors to more superficial locations within the solid tissue as in the prior art carries with it several drawbacks, including inter alia (i) reduced performance of or interference with the sensor due to, e.g., injection or introduction of various substances proximate to the epidermis, (ii) aesthetic considerations such as a visibly and tactilely detectable "bulge" of the sensor through the host's skin; (iii) susceptibility of the sensor and its components to deleterious external influences such as ballistic or other impingement, electromagnetic interference, etc.; and (iv) an increased propensity for the sensor to erode through the skin surface, leading to infection and a need to explant the device.

Prior art partially implantable sensors (e.g., those which include a percutaneous connection element and components worn external to the living being, such as the device 100 shown in FIG. 1), suffer from many disabilities, including without limitation (i) reduced wearer "body image" (i.e., the wearer is self-conscious of the apparatus on the exterior of their skin, such as when swimming, at the beach, etc.); (ii) discomfort for the wearer, including interference with clothing, "bulkiness"; (iii) pain due the device probe or sensor penetrating the skin to a subcutaneous location; (iv) increased risk of infection due to sensor penetration (e.g., "open" wound); and (v) susceptibility to damage or loss due to mechanical shock, acceleration, frictional forces on the user's skin (such as when swimming), loss of adhesion to the skin, or the like. Hence, such external sensing devices similarly are not optimized for monitoring of e.g., blood glucose, let alone for use for extended periods.

As such, there is a compelling need for a sensor designed to enable greater flexibility of implantation location and depth (including depths that avoid the foregoing disabilities and drawbacks associated with prior art implantable devices), as well as techniques for implanting the sensor in an optimized location and orientation so as to enhance its performance and longevity/viability within the recipient. Ideally, such apparatus and techniques would overcome the disabilities associated with each of the prior art fully implantable and partially implantable paradigms discussed above.

SUMMARY

The present disclosure satisfies the foregoing needs by providing, inter alia, improved methods and apparatus for implantation of a sensing or other electronic device within a living subject.

In one aspect, a miniaturized fully implantable sensor is disclosed. In one embodiment, the sensor comprises a plurality of oxygen-based glucose sensing elements disposed on a sensing region thereof, and is fabricated from biocompatible materials and uses biocompatible processes for sensing which advantageously mitigate or eliminate physiological responses from the host (e.g., FBR), and also dynamically accommodate any FBR which does occur algorithmically within the device. In one particular implementation, the miniaturized size, optimized shape, and biocompatibility of the sensor apparatus enable, inter alia, deeper and less traumatic implantation within the host's solid tissue (and subsequent extraction), thereby providing all of the benefits of an implantable sensor without the attendant disabilities of both prior art fully implantable and partially implantable devices and associated techniques.

In another aspect, a method of implantation of an electronic device such as a sensor is disclosed. In one embodiment, the method includes surgically implanting the sensor at a prescribed location (e.g., proximate to a fascial layer of the solid tissue of the host), as well as in a prescribed orientation so as to optimize one or more performance aspects of the sensor.

In another aspect, a method of enhancing the performance of an implantable electronic device is disclosed. In one embodiment, the device comprises a glucose sensor, and the method includes implanting the device within a host's solid tissue such that a sensing portion of the device is disposed so as to avoid or mitigate the effects of one or more sources of signal interference or degradation.

In yet a further aspect, methods of enabling and testing an implantable electronic device (e.g., the aforementioned sensor apparatus) are disclosed.

In a further aspect, methods of providing treatment to a living subject are disclosed.

In yet another aspect, a method of implanting a sensor apparatus in a living entity is disclosed. In one embodiment, the method includes obtaining a sensor; forming a cavity within a portion of tissue of the living entity, at least a portion of the cavity disposed proximate a subcutaneous fascial layer of the living entity; activating the sensor apparatus so that it can at least sense at least one physiological parameter, and transmit data wirelessly; disposing the sensor apparatus at least partly within the cavity so that the sensing region of the sensor apparatus is (i) situated immediately proximate the subcutaneous fascial layer and in direct contact with tissue proximate the subcutaneous fascial layer, and (ii) oriented with the sensing region substantially facing the subcutaneous fascial layer; and closing off the formed cavity such that the implanted sensor apparatus is substantially contained within, and operable to transmit the data wirelessly, within the living entity.

In one implementation, the sensor apparatus includes a power supply, a plurality of sensing elements disposed substantially within a sensing region of the sensor apparatus, signal processing apparatus in data communication with the plurality of sensing elements, and a wireless interface in data communication with the signal processing apparatus, the sensing apparatus configured for monitoring of at least one physiological parameter indicative of a glucose level within the living entity.

In another embodiment, the sensor is configured for monitoring of at least one physiological parameter, and the method includes: forming a cavity within a portion of tissue of the living entity; disposing the sensor at least partly within the cavity so that the sensor is situated in a desired position relative to at least one anatomical feature of the living entity; and closing off the formed cavity such that the implanted sensor is substantially contained and operable within the living entity.

In a further aspect, a method of providing therapy to a living being is disclosed. In one embodiment, the method includes: incising a portion of an abdomen of the living being; forming a cavity within a portion of the solid tissue of the living being accessible via the incising; disposing a sensor apparatus at least partly within the cavity so that the sensor apparatus is situated in a desired position and orientation relative to at least one anatomical feature of the living being; closing off the formed cavity such that the implanted sensor apparatus is substantially contained and operable within the living being; receiving wireless communications from the sensor apparatus; and injecting at least one therapy agent at a site on the abdomen at least proximate the incised portion.

In one implementation, the disposition of the sensor apparatus in the desired position and orientation cooperate to mitigate one or more deleterious effects on operation of the sensor apparatus resulting from the injecting of the therapy agent.

In yet another aspect, a method of providing treatment to a living being is disclosed. In one embodiment, the method includes: incising a portion of an abdomen of the living being; forming a cavity within a portion of the solid tissue of the living being accessible via the incising; disposing a first sensor apparatus at least partly within the cavity so that the first sensor apparatus is situated in a desired position and orientation relative to at least one anatomical feature of the living being; closing off the formed cavity such that the first sensor apparatus is substantially contained and operable within the living being; utilizing the first sensor apparatus to monitor at least one physiological parameter associated with the living being for a first period of time; subsequently re-incising the portion of the abdomen to explant the first sensor apparatus from the living being; disposing a second sensor apparatus at least partly within a cavity so that the second sensor apparatus is situated in a desired position and orientation relative to at least one anatomical feature of the living being; closing off the cavity so that the second sensor apparatus is substantially contained and operable within the living being; and utilizing the second sensor apparatus to monitor the at least one physiological parameter associated with the living being for a second period of time.

In another embodiment, the living being has a first sensor apparatus implanted at least partly within a cavity formed in the solid tissue of the living being, and the method includes: identifying an extant incision location on the living being, the extant incision having been previously used for implantation of the first sensor apparatus within the cavity; re-incising at least the extant incision location to explant the first sensor apparatus from the living being; disposing a second sensor apparatus at least partly within a cavity so that the second sensor apparatus is situated in a desired position and orientation relative to at least one anatomical feature of the living being; closing off the cavity so that the second sensor apparatus is substantially contained and operable within the living being; and utilizing the second sensor apparatus to monitor the at least one physiological parameter associated with the living being for a period of time.

In an additional aspect, sensor apparatus configured for implantation within tissue of a living being is disclosed. In one embodiment, the sensor apparatus includes: a substantially biocompatible housing; at least one sensing element disposed at least partly on an outer surface of the housing and configured such that the sensing element can sense at least one solute when placed in contact with at least a portion of the tissue; signal processing apparatus in signal communication with the at least one sensing element and configured to process signals generated by the at least one sensing element. In one implementation, the sensor apparatus is configured to be implanted within the tissue such that the sensor apparatus is disposed proximate a fascial or musculature layer of the living being, and operate with the at least one sensing element also proximate the fascial or musculature layer.

Other features and advantages of the present disclosure will immediately be recognized by persons of ordinary skill in the art with reference to the attached drawings and detailed description of exemplary embodiments as given below.

Figure 1:
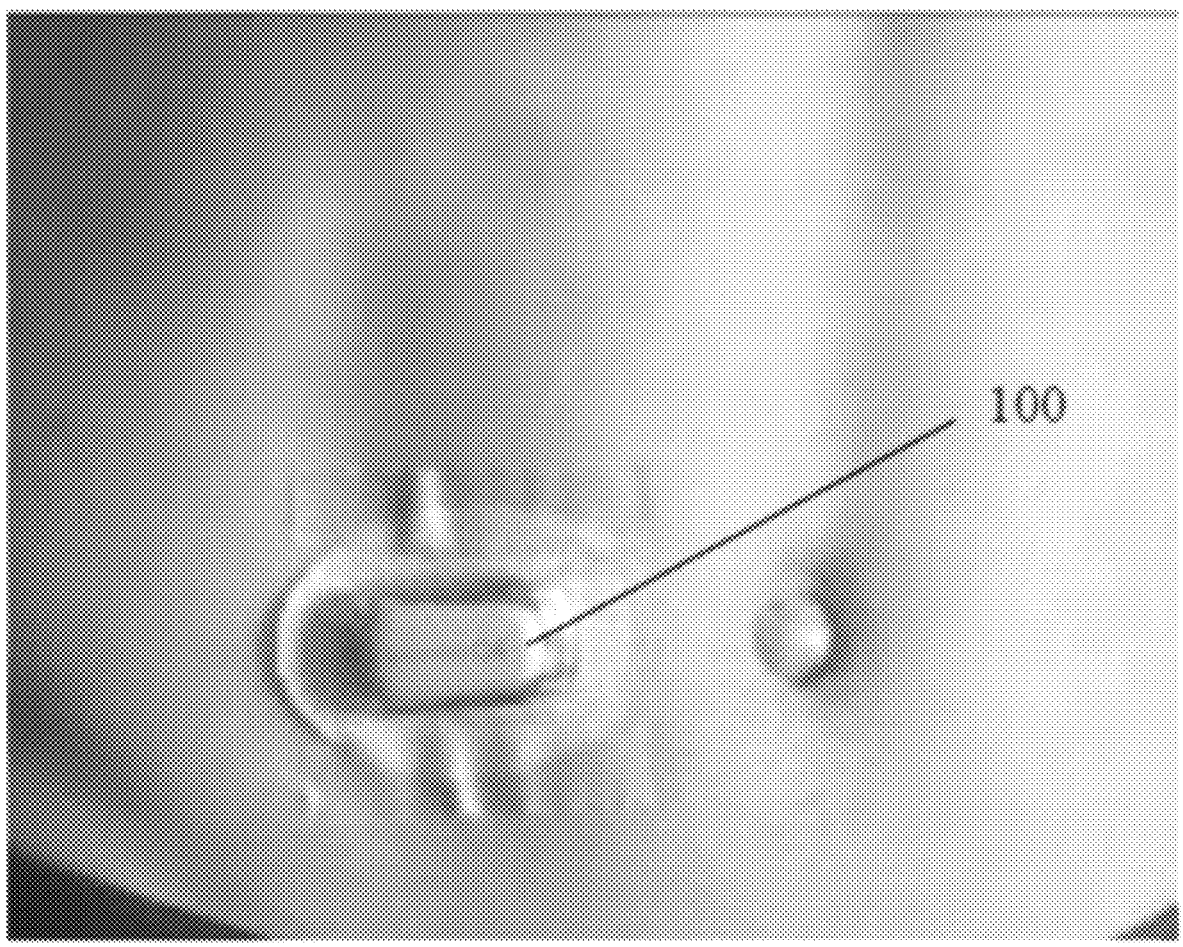
FIG. 1 is an illustration of a typical prior art external sensor apparatus (partially implantable glucose monitor), including typical placement on the abdomen of the host.

All Figures © Copyright 2015 GlySens Incorporated. All rights reserved.

DETAILED DESCRIPTION

Reference is now made to the drawings, wherein like numerals refer to like parts throughout.

Detailed Description of Exemplary Embodiments

Exemplary embodiments of the present disclosure are now described in detail. While these embodiments are primarily discussed in the context of a fully implantable glucose sensor, such as those exemplary embodiments described herein, and/or those set forth in U.S. Pat. No. 7,894,870 to Lucisano et al. issued Feb. 22, 2011 and entitled "Hermetic implantable sensor"; U.S. Patent Application Publication No. 20110137142 to Lucisano et al. published Jun. 9, 2011 and entitled "Hermetic Implantable Sensor"; U.S. Pat. No. 8,763,245 to Lucisano et al. issued Jul. 1, 2014 and entitled "Hermetic feedthrough assembly for ceramic body"; U.S. Patent Application Publication No. 20140309510 to Lucisano et al. published Oct. 16, 2014 and entitled "Hermetic Feedthrough Assembly for Ceramic Body"; U.S. Pat. No. 7,248,912 to Gough, et al. issued Jul. 24, 2007 and entitled "Tissue implantable sensors for measurement of blood solutes"; and U.S. Pat. No. 7,871,456 to Gough et al. issued Jan. 18, 2011 and entitled "Membranes with controlled permeability to polar and apolar molecules in solution and methods of making same," each of the foregoing incorporated herein by reference in its entirety, it will be recognized by those of ordinary skill that the present disclosure is not so limited. In fact, the various aspects of the disclosure are useful with, inter alia, other types of implantable sensors and/or electronic devices.

Further, while the following embodiments describe specific implementations of e.g., oxygen-based multi-sensor element devices, and specific protocols and locations for implantation (e.g., proximate the waistline on a human abdomen), those of ordinary skill in the related arts will readily appreciate that such descriptions are purely illustrative, and in fact the methods and apparatus described herein can be used consistent with, and without limitation: (i) other implantation locations; (ii) living beings other than humans; (iii) other types or configurations of sensors (e.g., peroxide-based glucose sensors, or sensors other than glucose sensors, such as e.g., for other analytes such as lactose); and/or (iv) devices intended to deliver substances to the body (e.g. implanted drug pumps, drug-eluting solid materials, and encapsulated cell-based implants, etc.); and/or other devices (e.g., non-sensors and non-substance delivery devices).

As used herein, the terms "health care provider" and "clinician" refer without limitation to providers of health care services such as surgical procedures, diagnosis, monitoring, administration of pharmacological agents, counseling, etc., and include for instance physicians, nurses, medical assistants, technicians, and can even include the user/patient themselves (such as where the patient self-administers, self-monitors, etc.).

As used herein, the terms "orient," "orientation," and "position" refer, without limitation, to any spatial disposition of a device and/or any of its components relative to another object or being, and in no way connote an absolute frame of reference.

Likewise, as used herein, the terms "top," "bottom," "side," "up," "down," and the like merely connote, without limitation, a relative position or geometry of one component to another, and in no way connote an absolute frame of reference or any required orientation. For example, a "top" portion of a component may actually reside below a "bottom" portion when the component is mounted to another device or object.

Overview

In one exemplary aspect, the present disclosure provides a methodology wherein a fully implantable, biocompatible sensor is disposed within a cavity or pocket formed within a living being (e.g., the frontal portion of a human, more specifically the abdomen, proximate the waistline), such that the sensor remains in a desired orientation and placement after the cavity or pocket is closed, so as to enhance the performance of the sensor (e.g., from an accuracy perspective), and also mitigate the effects of one or more factors potentially deleterious to the operation of the sensor and to the host being (e.g., human). The foregoing features enhance the robustness of the sensor, and ostensibly extend the time period over which the sensor may remain implanted and continue to provide useful data and signals.

In one implementation, the sensor comprises a somewhat planar biocompatible oxygen-based glucose sensor with multiple (e.g., 8) individual sensor elements disposed in a common sensing region on one side of the somewhat planar housing, which is implanted deep within the being's torso subcutaneous tissue proximate the extant abdominal muscle fascia, and optionally oriented so that the sensing region faces away from the being's skin surface (i.e., the plane of the sensor is substantially parallel to the fascia and the epidermis/dermis, with the sensing region facing inward toward the musculature under the fascia).

In one variant, the deep placement, orientation, and construction of the exemplary glucose sensor itself cooperate to enhance the performance of the sensor, especially over extended periods of time, with little or no external calibration.

Due in large part to the miniaturization and integration of the sensor, the foregoing implantation technique can advantageously be performed on an outpatient basis by a clinician using only local anesthetic. Recovery time from the procedure is minimal, and current implementations of the sensor apparatus have demonstrated longevity in vivo well in excess of one year.

Exemplary Implantable Sensor

Figure 2:
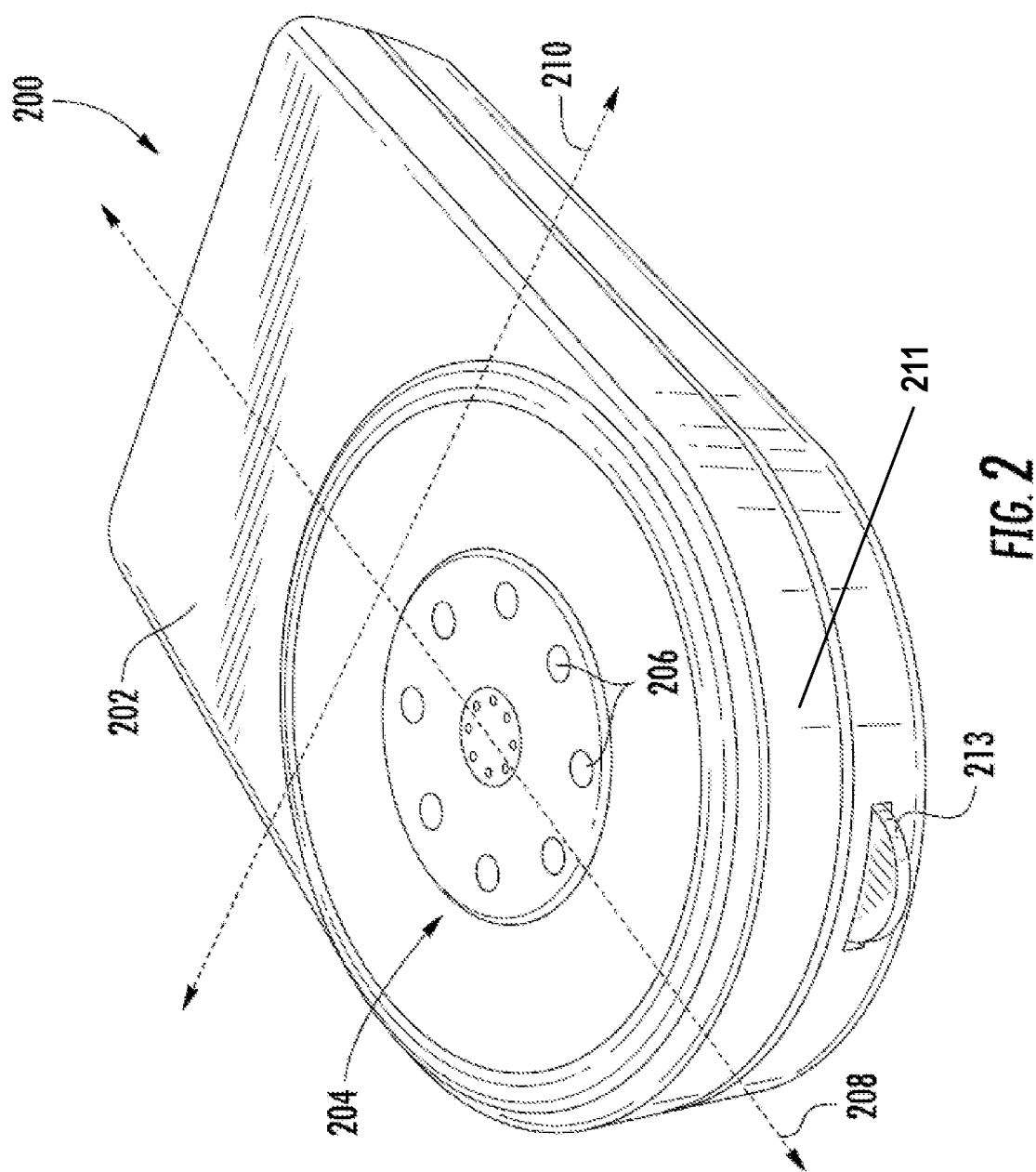
FIG. 2 is a front perspective view of one exemplary embodiment of a fully implantable sensor apparatus according to the present disclosure.
Figure 2A:
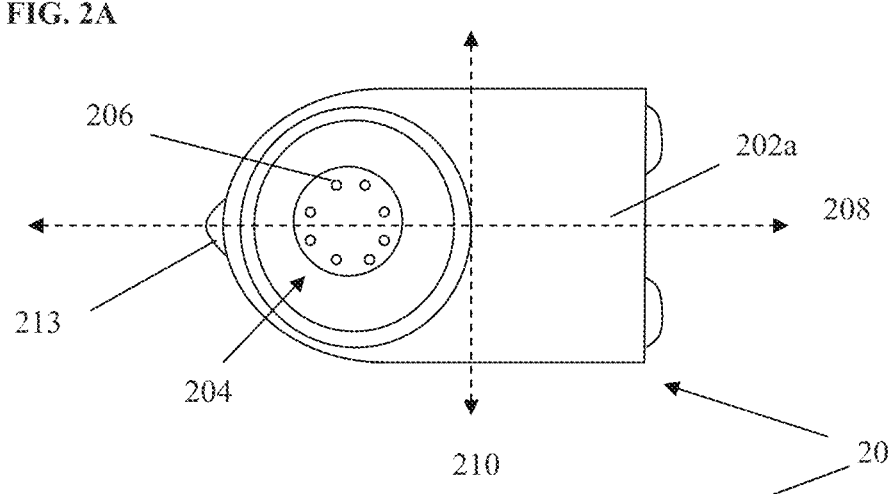
FIGS. 2A-2C are top, bottom, and side elevation views, respectively, of the exemplary sensor apparatus of FIG. 2.
Figure 2B:
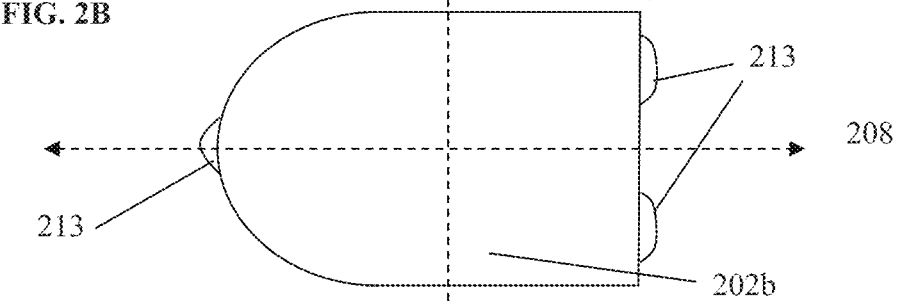
Figure 2C:
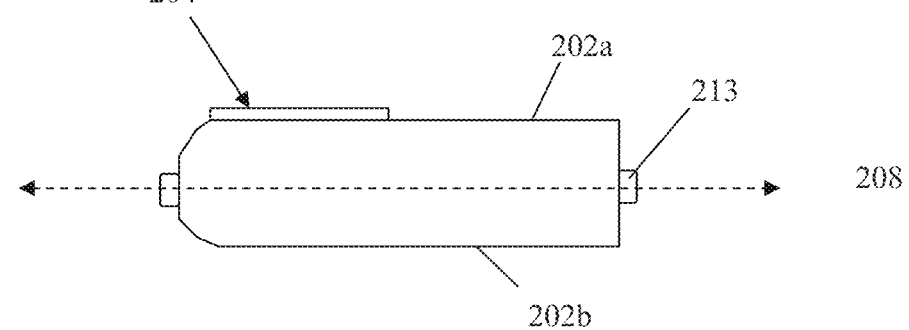

Referring now to FIGS. 2-2C, one exemplary embodiment of a sensor apparatus useful with various aspects of the present disclosure is shown and described.

As shown in FIGS. 2-2C, the exemplary sensor apparatus 200 comprises a somewhat planar housing structure 202 with a sensing region 204 disposed on one side thereof (i.e., a top face 202a). As will be discussed in greater detail infra, the exemplary substantially planar shape of the housing 202 provides mechanical stability for the sensor apparatus 200 after implantation, thereby helping to preserve the orientation of the apparatus 200 (e.g., with sensing region 204 facing away from the epidermis and toward the proximate fascial layer), resisting rotation around its longitudinal axis 208, and translation, or rotation about its transverse axis 210, which might otherwise be caused by e.g., normal patient ambulation or motion, sudden accelerations or decelerations (due to e.g., automobile accidents, operation of high-performance vehicles such as aircraft), or other events or conditions. Notwithstanding, the present disclosure contemplates sensor apparatus of shapes and/or sizes other than that of the exemplary apparatus 200, including use of means to maintain the desired orientation and position such as e.g., protruding tabs, "anchoring" the sensor apparatus to surrounding physiological structures such as the fascial layer by means of sutures or the like, and so forth.

It is also appreciated that depending on the type of sensor apparatus used, undesired movement (translation, rotation) of the sensor apparatus can be inhibited through physiological interaction of the sensor apparatus with the host subject at the site of implantation. For example, clinical trials of the exemplary apparatus 200 by the Assignee hereof indicate that some degree of tissue "contouring" with at least the sensing region 204 occurs over the duration of a typical implantation, due to inter alia normal biological processes within the host. In effect, the host's tissue closely contacts and develops contours directly reflective of the shape of the sensing region 204, thereby indirectly providing enhanced mechanical coupling (and attendant resistance to movement).

The exemplary sensor apparatus of FIGS. 2-2C further includes a plurality of individual sensor elements 206 with their active surfaces disposed substantially within the sensing region 204 on the top face 202a of the apparatus housing. In the exemplary embodiment (i.e., an oxygen-based glucose sensor), the eight (8) sensing elements 206 are grouped into four pairs, one element of each pair an active sensor, and the other a reference (oxygen) sensor. Exemplary implementations of the sensing elements and their supporting circuitry and components are described in, inter alia, U.S. Pat. No. 7,248,912, previously incorporated herein. It will be appreciated, however, that the type and operation of the sensor apparatus may vary; i.e., other types of sensor elements/sensor apparatus, configurations, and signal processing techniques thereof may be used consistent with the various aspects of the present disclosure, including, for example, signal processing techniques based on various combinations of signals from individual elements in the otherwise spatially-defined sensing elements pairs.

The exemplary sensor apparatus of FIGS. 2-2C also includes a plurality (three in this instance) of tabs or anchor apparatus 213 disposed substantially peripheral on the apparatus housing. As discussed in greater detail below with respect to FIGS. 3 and 3C, these anchor apparatus provide the implanting surgeon with the opportunity to anchor the apparatus to the anatomy of the living subject, so as to frustrate translation and/or rotation of the sensor apparatus 200 within the subject immediately after implantation but before any body response (e.g., FBR) of the subject has a chance to immobilize (such as via encapsulation) the sensor apparatus. In the illustrated embodiment, the tabs or anchor apparatus 213 each comprise a substantially closed loop through which the surgeon may optionally run a dissolvable suture or other such mechanism so as to effect the aforementioned anchoring. The closed loop may be formed e.g., at time of formation of the apparatus housing (e.g., when the housing is formed, molded, forged, or otherwise fashioned), or can be applied thereafter (e.g., via welding or brazing or adhesion of a wire loop or the like to the housing). It will be also appreciated that other configurations, numbers, and/or anchoring mechanisms may be used consistent with the present disclosure, as discussed in greater detail infra.

Various other construction details of the exemplary sensor apparatus 200 are described in U.S. Pat. No. 7,894,870 to Lucisano et al. issued Feb. 22, 2011 and entitled "Hermetic implantable sensor"; U.S. Patent Application Publication No. 20110137142 to Lucisano et al. published Jun. 9, 2011 and entitled "Hermetic Implantable Sensor"; U.S. Pat. No. 8,763,245 to Lucisano et al. issued Jul. 1, 2014 and entitled "Hermetic feedthrough assembly for ceramic body"; U.S. Patent Application Publication No. 20140309510 to Lucisano et al. published Oct. 16, 2014 and entitled "Hermetic Feedthrough Assembly for Ceramic Body"; U.S. Pat. No. 7,248,912 to Gough, et al. issued Jul. 24, 2007 and entitled "Tissue implantable sensors for measurement of blood solutes"; and U.S. Pat. No. 7,871,456 to Gough et al. issued Jan. 18, 2011 and entitled "Membranes with controlled permeability to polar and apolar molecules in solution and methods of making same", each of the foregoing incorporated herein by reference in its entirety.

As noted above, one embodiment of the sensor apparatus 200 is configured for so-called "deep" implantation within the solid tissue of the subject (e.g., low on the frontal abdominal region), approximately at the level of the deep/muscle fascial layer. As is known, a fascia is a band or sheet of connective tissue fibers, primarily collagen, disposed beneath the skin, and which functions to attach, stabilize, enclose, and separate muscles and other internal organs. Fasciae are classified according to their distinct layers as in superficial fascia, deep (or muscle) fascia, visceral and parietal fascia, and by their functions and anatomical location. Like ligaments, aponeuroses, and tendons, fasciae are made up of fibrous connective tissue containing closely packed bundles of collagen fibers oriented in a wavy pattern substantially parallel to a direction of pull. The collagen fibers are produced by the fibroblasts located within the fascia. Fasciae are accordingly flexible structures able to resist great unidirectional tensile forces.

As will be described subsequently herein, exemplary disposition of the sensor apparatus 200 at the deep muscular fascial level provides several benefits both from the perspective of the user (patient) and the clinician (e.g., surgeon).

Methods for Implantation

Figure 3:
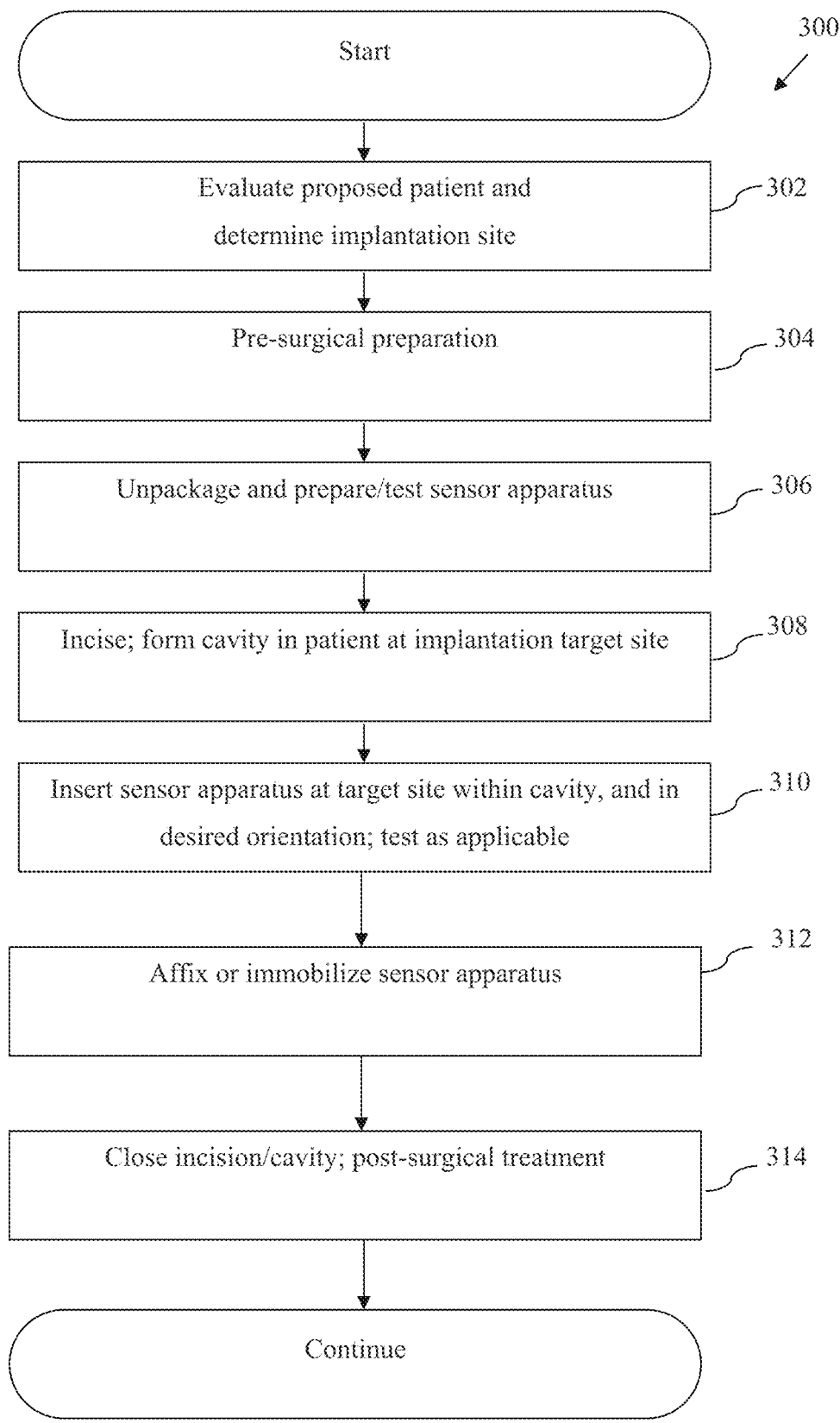
FIG. 3 is a generalized logical flow diagram illustrating an exemplary embodiment of a method of electronic device implantation in accordance with the present disclosure.

Referring now to FIG. 3, methods of implantation of one or more sensors, and treatment of a living being, are described in detail.

As shown in FIG. 3, one exemplary embodiment of a method 300 of implantation of a sensor is disclosed. At step 302, the patient (e.g., human being) is evaluated for: (i) the propriety of use of the implantable sensor (e.g., whether contraindications or other factors make the use of the particular sensor impractical or undesirable); (ii) the best or desired implantation site (which, as discussed elsewhere herein, may or may not be a previously utilized site); and (iii) any other factors which the heath care provider should consider, such as recent other surgeries, recent ingestion of pharmacological agents, and the like.

At step 304, the patient is prepared for surgery (whether traditional, laparoscopic, or otherwise). Such preparation may include for example placement in a surgical environment (e.g., operating or treatment room), disinfecting the surface of the skin at and proximate to the incision site, (such as using Betadine® or similar topical microbicide), administration of pharmaceuticals or other agents for, e.g., anesthetization of the implantation area via local anesthetic, sedation of the patient via various sedating agents, anesthetization of the patient (generally) via a general anesthetic, administration of a prophylactic dose of an antibiotic compound, or the like.

The incision site(s) may also be marked on the patient at this point. In one variant, the incision site, as well as the desired extent of the pocket to be formed (discussed below) may be marked to aid the surgeon during the implantation procedure. A typical incision length for the sensor apparatus of FIG. 2 is on the order of 2.5 cm, although greater and lesser lengths are contemplated by the present disclosure depending on, e.g., the actual size and shape of the implanted device, particular anatomical features or considerations relating to the patient, etc.

At step 306, the sensor is prepared for surgical implantation in the patient. In one embodiment, the exemplary sensor apparatus 200 of FIG. 2 herein is utilized, although as previously discussed, any number of types and/or configurations of sensors may be used consistent with the method 300. In the case of the sensor apparatus 200 of FIG. 2, the sensor includes a sensing region 204 disposed on one side of the substantially planar sensor apparatus housing, through which all glucose monitoring is conducted when the sensor apparatus is in vivo. The sensor apparatus 200 is (i) removed from its packing/shipping container, preserving its sterility after removal and before implantation, (ii) powered up, and (iii) functionally tested so as to assure its operability in certain regards.

Figure 3A:
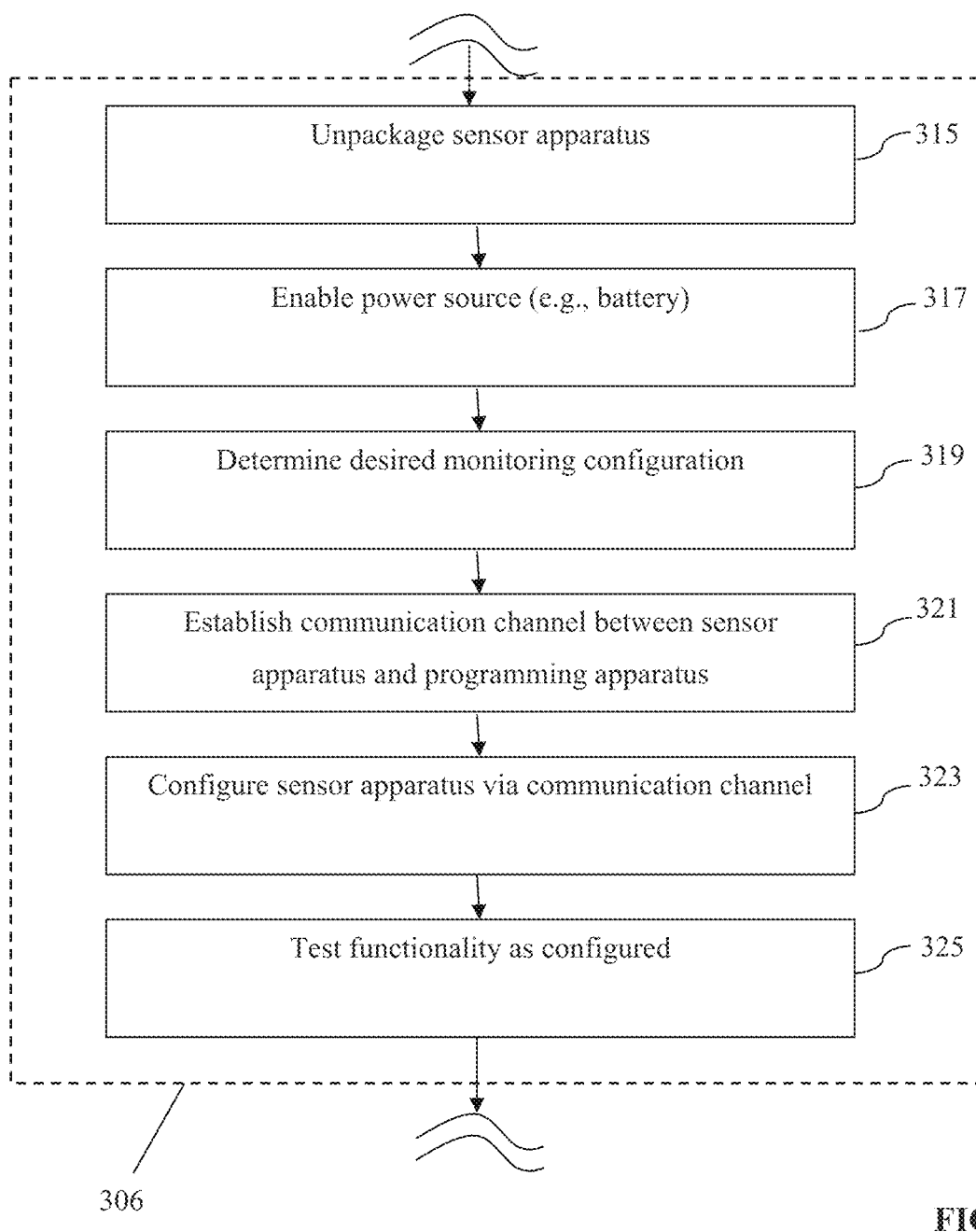
FIG. 3A is a generalized logical flow diagram illustrating an exemplary embodiment of a method of preparing a sensor apparatus for implantation in accordance with the present disclosure.

FIG. 3A illustrates one exemplary methodology for carrying out step 306 of the method 300. As shown in FIG. 3A, the sensor apparatus is first removed from its storage/packing container as noted above (step 315). Next, the power supply of the apparatus is enabled, such as by inserting or enabling electrical contact with a battery of the apparatus (step 317). Where the power supply of the apparatus requires energizing by an outside electrical field (e.g. where power is to be delivered to the device by inductive coupling), an appropriate external apparatus is utilized.

Next, per step 319, the desired configuration for the particular application (e.g., analyte monitoring selection, wireless interface parameters, sensing/data transmission frequency, etc. for a given patient) may be determined (as applicable). It is noted that while the exemplary methods of FIGS. 3-3A illustrate determination of such a configuration, the present disclosure contemplates any number of other options, including utilizing a fully pre-programmed sensor apparatus (e.g., with no required or possible user configuration), so as to inter alia, simplify the preparation and implantation of the apparatus, and avoid any potential programming or configuration errors, thereby obviating at least step 319.

Per step 321, a communication channel is established between the signal processing/microcontroller architecture of the sensor apparatus and an external device, such as via a wireless "command" channel and protocol. Similarly, a wired (e.g., micro-USB) form factor can be used along with a serialized bus protocol such as I²C, PCIe, etc. While wireless communication with the sensor apparatus may be desired for many cases, the wired implementation may also be constructed such that the physical interface is shielded after completion, internal to the sensor apparatus, or otherwise adapted so as to preclude any ingress of biological matter into the apparatus housing, or conversely any egress of substances from inside the device housing into the surrounding tissue of the patient.

A properly configured external device (e.g., tablet computer, smartphone, desktop/laptop, flash drive, etc.) can be used to transmit commands to the sensor apparatus once the channel is established, according to the prescribed command protocol.

Per step 323, the command channel established in step 321 is utilized to configure the sensor apparatus, which may include "flashing" the non-volatile storage within the device with new firmware, configuring one or more user-selectable parameters or options, and the like.

Per step 325, the configured device is then tested to assure proper programming/functionality prior to implantation (although some testing can be accomplished after implantation, as described elsewhere herein).

Note that in one embodiment, the sensor is entirely pre-programmed, and is configured to transmit "raw" data signals off-sensor to a receiver (the latter enabling subsequent processing of the raw data signals). However, in certain other embodiments, the sensor apparatus can optionally be configured with a plurality of capabilities such that a user (e.g., health care provider) can selectively enable or disable features for the current patient/application, thereby in effect customizing the sensor apparatus for the application. For instance, in one variant, the sensor apparatus might include algorithms or signal processing applicable to a particular operational context (e.g., sensing of multiple ones of certain analytes), but which are not appropriate for the current application or patient due to their physiology, age, type of medical condition/diabetes, etc. Similarly, electronic design factors may form a basis for the selective configurability, such as e.g., where the sensor apparatus is fitted with multiple wireless air interface types and/or frequency bands, modulation/coding schemes (MCS), etc., all of which may not be needed after implantation. For instance, in one option, due to extant interference by virtue of the patient's job, residence location, prevailing environment, etc., certain wireless frequencies (e.g., different frequencies within the ISM band) or types of interfaces (e.g., OFDM versus direct sequence versus narrowband/FDMA) may be more desirable than others, and hence can be selected at time of implantation (subject to regulatory restrictions and requirements), with non-selected options shut off or put to sleep so as to conserve electrical power within the implanted device after implantation, thereby extending its viability in vivo. In this regard, the clinician can optionally be given a menu of choices in terms of device configuration from which to select so as to readily optimize the implantation for that given patient, without having to employ a single-function or particular device configuration which may or may not be available to the clinician at that particular surgical location and/or point in time.

Moreover, the aforementioned optional configuration of the device can be accomplished when the device is in vivo, such as after a trial period. For example, in one variant, the implantation "lifetime" of the sensor apparatus may be extended (assuming suitable physiological monitoring performance continues) by selectively shutting down or powering off various features, functions or components of the implanted sensor, reprogramming (e.g., download of new firmware which further optimizes operation, etc.), such as via wireless command to the signal processor/microcontroller of the device. Hence, what was ostensibly a 12-month implantation period may be extended by selective in vivo reconfiguration of the device in order to optimize power consumption. As is well known, digital processors and wireless baseband processors each may employ multiple different power planes and "sleep" states which progressively reduce power consumption by the device, depending on the operation demands on the device. If it is determined that, e.g., the frequency of calculations or sensor samplings can be reduced later in the life of a given implementation (such as where the host becomes more familiar with his/her own monitoring, response to certain ingested foods or liquids, etc.), it may be that the "tempo" of operation of the sensor apparatus can be reduced, providing attendant power consumption reduction. For instance, in the context of the exemplary sensor apparatus 200 of FIG. 2, the sensor apparatus includes multiple (4) sets of sensing and reference sensing elements, which are in one implementation adapted to dynamically compensate for e.g., FBR or other so-called "confounding factors" occurring proximate the sensing elements (see, inter alia, U.S. Pat. No. 7,248,912 previously incorporated herein, for a discussion of various such factors), thereby maintaining the accuracy of the device as a whole. Accordingly, as sensing elements or sets thereof become inoperative or unreliable, these elements/sets can be selectively removed from the signal processing logic and deactivated, thereby conserving electrical power, and ostensibly extending the implantation lifetime of the sensor apparatus in that given patient.

Using the foregoing approach of a reconfigurable sensor apparatus, the cost and inventory burden associated with the sensors is reduced, since in effect a "one size fits all" device can be stocked for use across a wide variety of potential applications. It will be appreciated, however, that the various aspects of the disclosure can be practiced with equal success using unique or heterogeneous sensor apparatus or electronic devices across different patients, including for instance having variations in size or shape (e.g., adult and juvenile sizes), sensing capability/configuration (multiple analytes for certain types of patients, a single analyte for others), communications and/or data processing capabilities, etc.).

It will be appreciated that while the aforementioned embodiment of the methodology powers up and checks the functionality of the device (and optionally enables/disables features of the sensor) prior to implantation, one or more of these procedures can be performed when the device is in vivo (including after the surgical implantation procedure is complete) if desired. For example, in one such variant, the sensor is powered up prior to implantation (since a power circuit or battery malfunction generally cannot be rectified after implantation), yet is not "configured" for operation and tested until it is disposed at its target implantation location deep within the patient's tissue. This approach can advantageously be utilized to, inter alia, both (i) test the sensor in the actual environment which it will be subsequently used (as opposed to merely in "open air" or its sterile shipping/packing environment, each of which may not allow the tests with appropriate sensory input signals as compared to being in vivo with the sensor active sensing region 204 in contact with the patient's tissue) and (ii) obtain representative signal inputs (e.g., from the sensor's sensing array) and outputs (e.g., wireless signals of insufficient strength may be attenuated by the patient's tissue, such attenuation which could not be accurately assessed before the sensor was placed beneath the tissue).

Testing performed on the sensor apparatus may include for example: (i) battery voltage or current checks; (ii) wireless interface checks such as transmission of test data or actual sensed data; (iii) functional command checks, such as where a command is wirelessly transmitted to the device in order to cause the sensor apparatus to perform a function, reconfigure itself, transmit data, etc.

Figure 4:
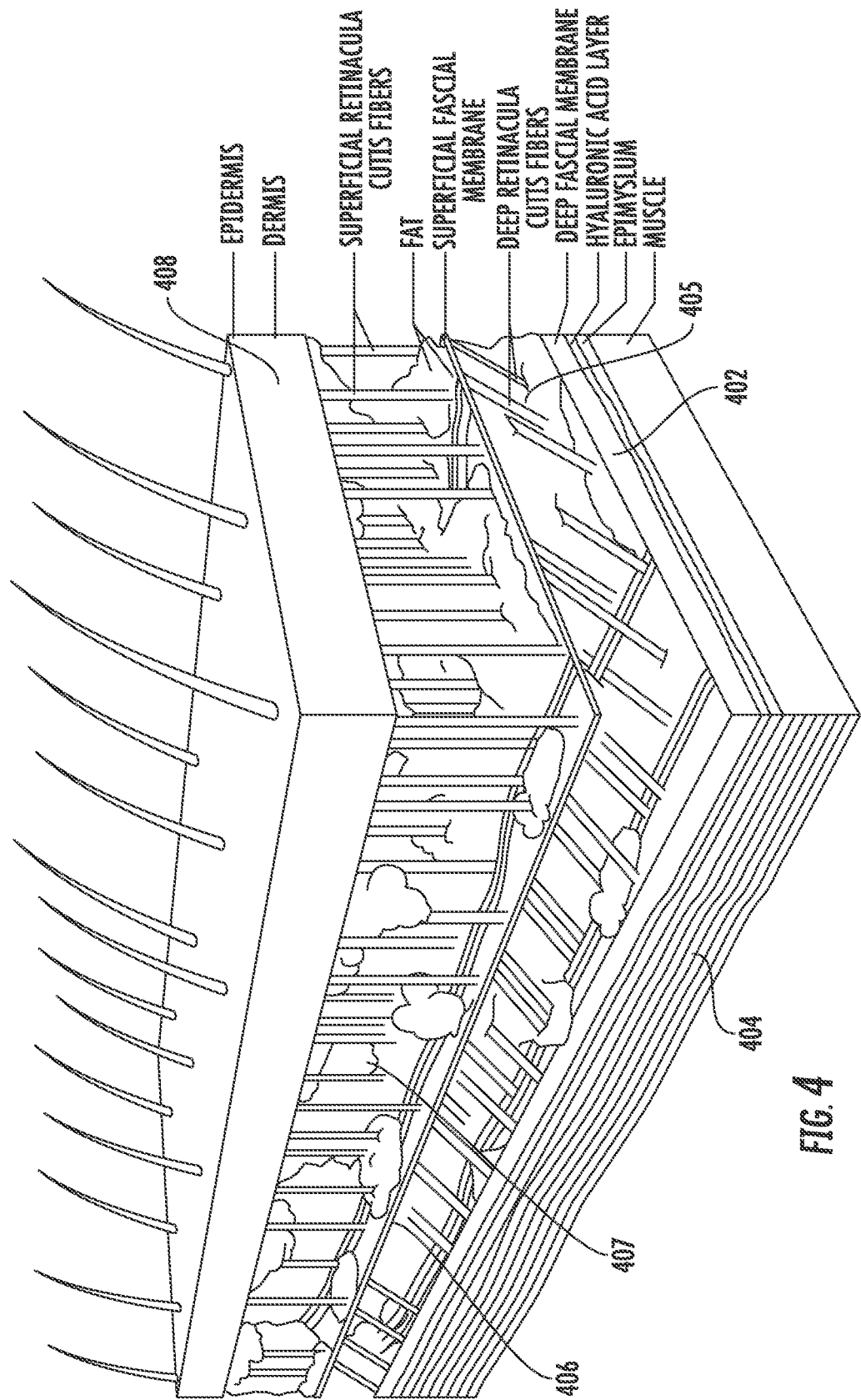
FIG. 4 is perspective cross-sectional view of abdominal "solid tissue" of a typical human being, showing the various components and layers thereof, including fascial layers.

Referring again to FIG. 3, at step 308 of the method 300, the patient is surgically incised at the target location (e.g., in the lower abdomen, lateral to the midline, inferior to the umbilicus and superior to the inguinal ligament, and a cavity formed below the skin and extending to the fascia underlying the target location. In one variant, the user's superficial (scarpal) fascia is incised, and the adipose tissue 405 immediately proximate the deeper fascial membrane 402 (i.e., anterior abdominal fascia; see FIGS. 4 and 5) is merely separated from the fascial membrane so as to form the desired cavity or pocket 502, with little or no tissue removal from the patient. Such separation is preferably performed using "blunt" techniques (i.e., without cutting per se), to minimize tissue and blood vessel trauma, and also mitigate prospective FBR (which may be exacerbated from cutting versus blunt formation), but may also be performed using an instrument such as a scalpel or surgical scissors if needed or desired for other reasons. In an alternate variant, the surgeon may remove a small amount of fat cells or tissue in the region in order to accommodate the volume of the sensor apparatus. In yet another variant, a specialized "pocket forming" surgical tool may be inserted into the location where the pocket is desired, and then removed to create a suitable pocket.

In one exemplary embodiment of the method 300, the pocket is formed in a substantially vertical direction relative to the (substantially transverse) incision; i.e., the incision is formed low on the patient's abdomen, and the pocket is formed internally with a longitudinal axis thereof pointing roughly towards the patient's head or upper abdomen.

As noted supra, the target implantation site is in one implementation chosen to be in the patient's lower abdomen, lateral to the midline, inferior to the umbilicus and superior to the inguinal ligament. While other sites may be used consistent with the present disclosure, this site often has significant advantages associated therewith, both for the implanting surgeon and the patient. Specifically, in obese individuals (or even those merely with a significant amount of fat around their midsection), implantation is typically less traumatic and invasive at the aforementioned target location, since the thickness of the fatty tissue layer in such individuals declines rapidly as a function of proximity to the groin area. Hence, less damage to the patient's tissue and blood vessels occurs when performing implantation in this region.

Moreover, in combination with the aforementioned formation of the cavity in a generally "vertical" direction upward from the incision, such incision location advantageously affords the surgeon the ability to implant the sensor apparatus 200 deeply within the patient's abdomen (with all of the attendant benefits thereof), yet with minimal tissue and blood vessel trauma.

It is also appreciated that from an aesthetic perspective, placement of the incision low on the patient's abdomen can be highly desirable, so as to put the resulting scar out of normal view (e.g., below the "bikini line" or such).

Figure 5:
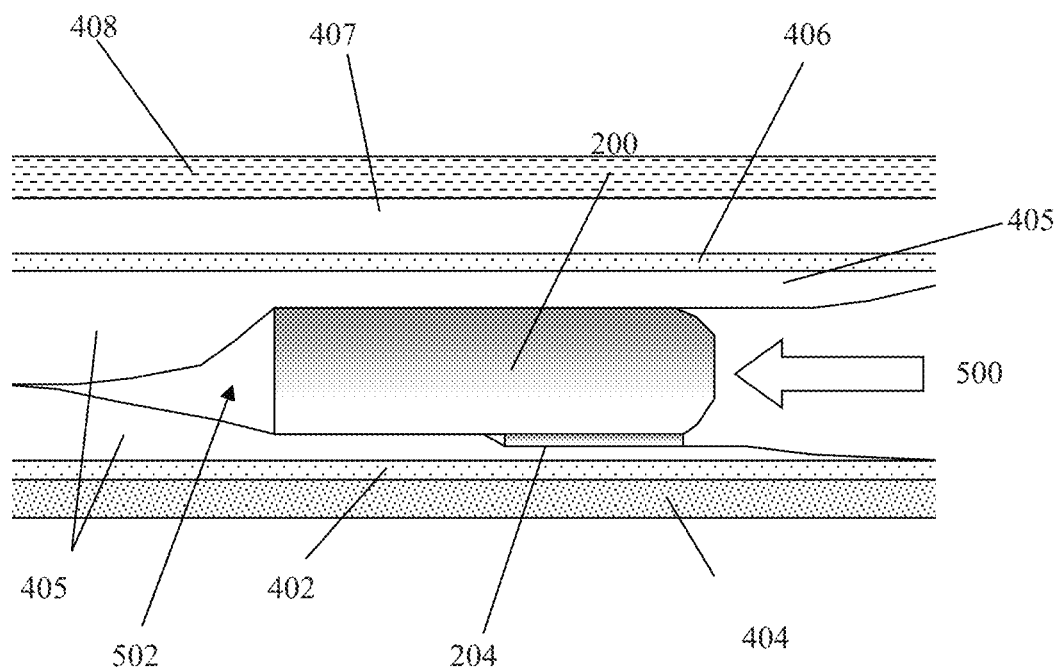
FIG. 5 is side cross-sectional view of an exemplary sensor apparatus implanted within a cavity or pocket formed in the tissue of FIG. 4, and proximate to the muscular fascia thereof.

Once the cavity or pocket 502 (FIG. 5) is formed, the sensor apparatus 200 is implanted within the cavity/pocket in the direction 500 shown, so that the sensing region 204 is both proximate the target fascial layer and oriented in the desired direction (step 310). As discussed supra, the somewhat planar shape of the sensor housing 202 helps to maintain the desired sensor orientation and placement; accordingly, the sensor apparatus 200 in the present embodiment of the method 300 is inserted into the cavity 502 with the "flat" sides substantially parallel to the plane of the fascial layer 402, musculature 404, superficial fascia 406, superficial fatty tissue layer 407, and epidermis 408, as shown in FIG. 5. In one variant, the sensor apparatus 200 is oriented "round side up", such that the rounded end 211 (see FIG. 2) is inserted into the formed pocket first, thereby aiding in placement with minimal friction and effort.

Per step 312 of the method 300, the sensor apparatus 200 can optionally be affixed or "anchored" to the patient's anatomy so as to, inter alia, preclude the sensor apparatus from moving or dislocating within the patient after implantation (and potentially affecting the operation of the sensor apparatus, such as by changes or failure of the tissue coupling to the sensing elements of the apparatus). In one such variant, sutures are used in conjunction with one or more anchor points or tabs 213 formed or disposed on the outer surfaces of the sensor apparatus 200 (see FIGS. 2 and 3C), such that the sensor apparatus can be sutured to the patient's underlying fascia (e.g., anterior abdominal fascia) or other anatomical feature(s) within or proximate to the formed pocket in the desired location and orientation. In one variant, dissolvable sutures of the type well known in the medical arts are used for such purpose, thereby enabling the sensor apparatus to be secured within the patient until FBR and/or other natural body processes perform this function. Use of the dissolvable sutures provides, inter alia, for easier subsequent explant, since the sutures will have completely dissolved by time of explant (e.g., a year or 18 months from implantation), thereby obviating having to surgically sever and remove them. Notwithstanding, it will be appreciated that non-dissolvable sutures (and/or other anchoring or securing means, such as e.g., (polyester velour) fabric patches or tabs, or the like) may be used consistent with the present disclosure as desired.

Figure 3B:
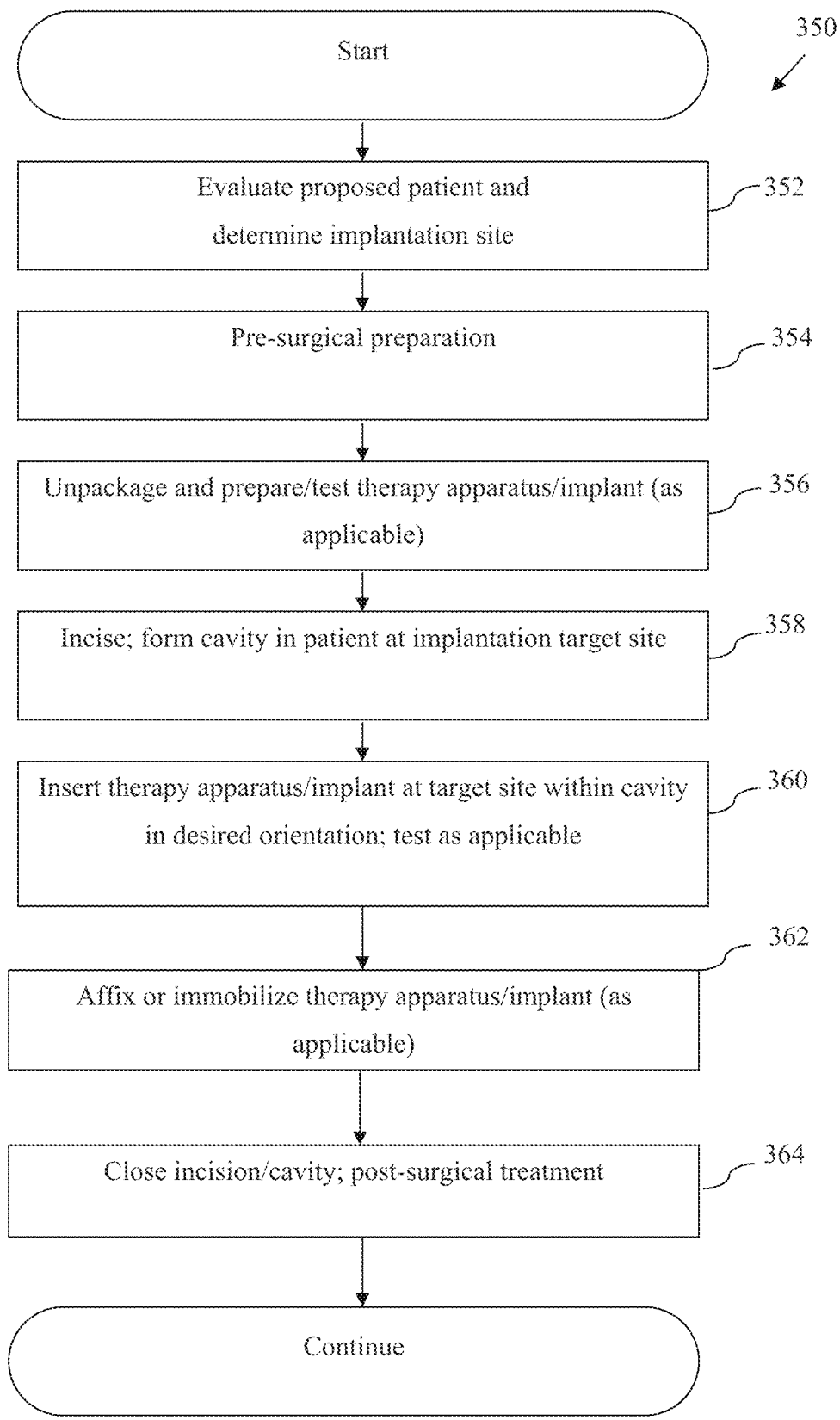
FIG. 3B is a generalized logical flow diagram illustrating an exemplary embodiment of a method of therapy device or material implantation in accordance with the present disclosure.
Figure 3C:
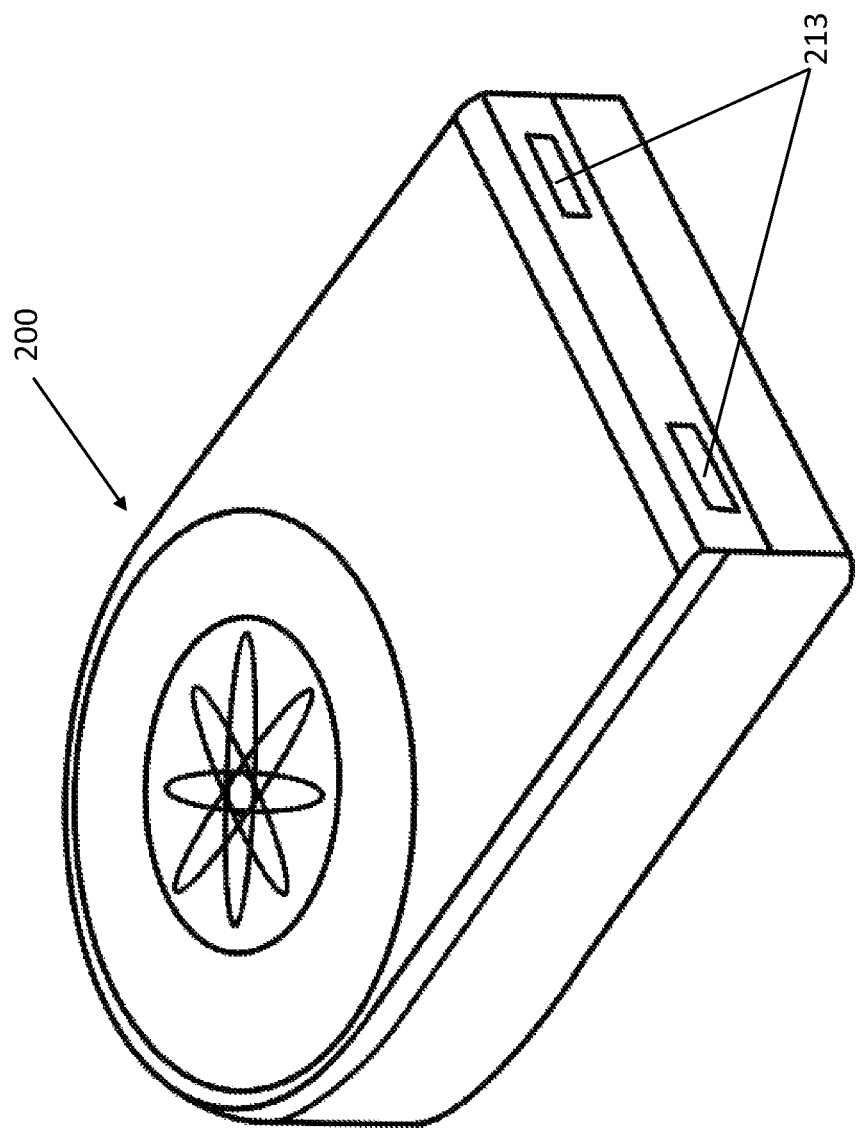
FIG. 3C is a rear perspective view of an exemplary embodiment of the sensor apparatus, including one or more attachment or anchoring apparatus.

It is also noted that while the exemplary sensor apparatus embodiment (e.g., as shown in FIGS. 2 and 3C) has three (3) anchor points or tabs 213 (i.e., one on the front "rounded" portion as shown in FIG. 2, and two on the rear "squared" portion as shown in FIG. 3C), more or less may be used. While the present disclosure contemplates use of no anchoring means (e.g., allowing the sensor apparatus 200 to "float" within the pocket, the latter which is closed or otherwise configured so as to maintain the desired placement of the sensor apparatus after implantation), or a single anchor (e.g., a single suture or other means with a single tab 213 on one side or end of the sensor apparatus, so as to at least partly constrain the sensor within the pocket 502), two (2) or more anchors, ideally spaced apart at some distance from each other relative to a characteristic dimension of the sensor apparatus, is considered optimal in many cases so as to frustrate potential "flipping" of the sensor apparatus within the pocket, especially when the pocket is not completely or partly closed off (e.g., before the normal FBR has had an opportunity to establish encapsulation) after implantation; this approach is especially useful in highly active individuals where, by nature of aggressive or jarring physical motion (such as mountain bike riding, playing contact sports, gymnastics, etc.), such undesired movement of the sensor apparatus within the pocket is more likely to occur.

Lastly, per step 314 of the method 300, the surgical incision (and optionally the cavity itself) are closed, and post-surgical treatment is applied to the patient. In one variant, the surgical incision is closed (e.g., via suturing, surgical tape or adhesive, and/or surgical staples) such that scarpal fascia and skin (lower inverted layer and higher layer) are closed, yet the formed pocket 502 is not affirmatively closed off (e.g., sutured), so as to reduce trauma to the patient and ostensibly facilitate later explant. Alternatively, the pocket 502 may be partly or fully closed off, such as via the aforementioned suturing or other means (e.g., dissolvable surgical tape or patch). Providing such "deep" as well as surface layer wound closures may be helpful in aiding healing and avoiding subsequent compromise of the closed wound, especially in individuals where their particular anatomy and anticipated activity profile might otherwise place undue stress on a single-layer closure.

The exemplary "deep implantation" approach of the present disclosure provides, inter alia, reduced sensitivity to or possibility of interference from injections or biological processes which may occur at or near the dermis/epidermis, and further provides some degree of enhanced "mechanical" shielding or ballistic protection for the potentially more delicate sensing region by virtue of both (i) the layer of tissue, etc. interposed between the sensor and the patient's epidermis, and (ii) the orientation of the sensing region away from any external forces which may impinge on the patient's abdomen, such as a missed baseball or football catch, steering wheel in an automobile accident, or the like. Additionally, the present disclosure contemplates the implantation of a biocompatible shield, which may be a rigid ceramic or the like plate or cup-shaped element, or may comprise a compliant material such as silicone rubber, which can be disposed immediately proximate the sensor apparatus or at a tissue layer closer to the epidermis, and which can provide additional ballistic or impingement protection for the sensor apparatus when implanted, such as for patients who engage in contact sports, military, or law enforcement activities, or the like.

Further, implantation of the sensor apparatus at a greater subcutaneous depth (i.e., proximate the muscular fascia) reduces or even eliminates any visible protrusion of the subject's abdomen, thereby making the sensor apparatus effectively invisible to the external observer.

Further, implantation of the sensor directly proximate a muscle fascia layer enhances the availability of solutes to the sensor, as the sensor is closer to the rich vascular bed associated with the underlying muscle. This enhanced solute availability advantageously supports increased solute flux to the sensor and thereby increased magnitudes of sensor signals and signal-to-noise ratios, enhancing sensor accuracy and performance. Shallow implantation further may result in reduced or insufficient access to blood oxygen levels, thereby reducing the effective range of the device in measuring blood glucose; conversely, the "deep" implantation described herein affords enhanced access to oxygen, and accordingly extends the dynamic range of the device, which results in, inter alia, enhanced operational flexibility (including enhanced time before explant is required).

Further, deeper implantation sites are associated with more stable, less fluctuating temperatures, which is of advantage for sensor types that possess temperature dependency.

Further, deeper implantation reduces risks for erosion of the sensor through the skin, the risk for which would otherwise be exacerbated by proximity of the sensor to the epidermis and exposure to external mechanical forces.

It will also be appreciated that in the exemplary embodiment of the sensor apparatus (FIG. 2, et seq), the sensing elements are disposed substantially on an opposite face or side from the (internal) radio frequency transmitter/transceiver antenna (not shown), such that emissions from the latter (such as via primary or ancillary lobes of the radiation pattern used for signal transmission) are substantially directed outward from the patient and away from the sensing elements (and supporting electronics within the sensor housing, such as an analog "front end" circuit used to receive signals from the sensing elements in one implementation), thereby mitigating electromagnetic noise or interference (EMI) in the sensing circuitry from antenna emissions.

Selection of the exemplary location near the muscular fascial layer 402 advantageously also requires only minimal surgical intervention (e.g., outpatient procedure or the like performed by a general surgeon or similar clinician versus a specialist), since the fascial layer in the exemplary embodiment is not penetrated or incised. Accordingly, only a small incision is necessary (e.g., approximately one to one-and-one-half inches long based on the current implementation of the sensor apparatus), and the entire procedure generally can be completed in less than 15 minutes.

Moreover, it is contemplated by the inventors hereof that the degree or level of FBR within the patient may be directly or indirectly related to the depth of implantation of a given implant (e.g., sensor), such that implantation of such a device at one depth may result in a differing type and/or magnitude of FBR than would occur for the same device implanted at a different depth in the same patient at the same location. Accordingly, the present disclosure contemplates, in one embodiment, use of such relationship as a factor in considering a depth of surgical implantation. For instance, in the case where anecdotal or other data indicates that FBR is reduced or ameliorated in severity or type as depth of implantation increases, such information may be used in selecting a target location and depth for the sensor apparatus or other implanted device. As noted above, prior art approaches to implantation generally consider only "shallow" implantation and/or implantation so as to maintain a prescribed relationship to the patient's external (dermal) layers.

It will also be appreciated that while the foregoing methodology is described substantially in terms of use of a deep or musculature fascial layer, a more superficial fascial or other layer may in certain cases be used (so as to minimize trauma and recovery time of the subject by not incising or cutting through the superficial fascial layer, while simultaneously providing good sensor performance and the other benefits described herein).

For example, it is contemplated that further miniaturization of the sensor apparatus will occur over time (e.g., as electronics, power sources, etc. are further integrated and reduced in size), such that a smaller incision and smaller/shallower "pocket" can be used for implantation.

Additionally, the present disclosure contemplates other potential implantation sites, including for example those yet deeper within the patient's anatomy than the exemplary embodiments previously described. For instance, it may be desirable in certain cases to incise through the deeper anterior abdominal fascia referenced above and form the pocket 502 within tissue on the interior side thereof, such as in the case of patients with friable skin structures, or where further protection of the implantable device is desired, or where perfusion of the tissue layers otherwise accessible to the device in the previously described exemplary embodiments is inadequate. In such cases, the preferred orientation of the device would be such that its active face (i.e. the face that required access to perfused tissue) would be adjacent to the fascia layer on which the device was being located. For instance, in one such variant of the implantation method, the sensor apparatus 200 of FIG. 2 is disposed at the previously discussed implantation site and with sensor-face outward (i.e., facing the muscular fascia, but from the interior side), and radio frequency energy is transmitted substantially through the subject toward their back (and thereby maintaining a high level of "noise" isolation between the RF interface and the electronics of the sensor elements). In another configuration of the sensor 200 adapted for such instances, the radio frequency transceiver/antenna may be configured to transmit RF energy through the same sensor apparatus housing face as the sensor; e.g., with reduced RF power so as to mitigate any possible noise or interference issues with the disposition of the RF transceiver/antenna on or under the same face of the apparatus housing as the sensor elements. Various other configurations will be appreciated by those of ordinary skill given the present disclosure.

It is also envisaged that as circuit integration is increased, and component sizes (e.g., lithium or other batteries) decrease, and further improvements are made, the sensor may increasingly be appreciably miniaturized, such that successively smaller and smaller incisions are required for implantation of the sensor apparatus over time. Laparoscopic implantation, or even a coarse "injection" delivery by trocar are also feasible methods of implantation with appropriate adaptation, such adaptation being well within the skill of an ordinary artisan in the medical or surgical arts when given the present disclosure.

As previously noted, the "deep" implantation technique of the present disclosure can also be utilized not only for other types of sensors, but also for apparatus and/or materials other than sensors, including for example devices intended to deliver substances to the body (e.g. implanted drug pumps, drug-eluting solid materials, and encapsulated cell-based implants, etc.), and/or other devices for which implantation may be desired. FIG. 3B shows an exemplary embodiment of a method of implantation of such non-sensor apparatus. As shown in FIG. 3B, one exemplary embodiment of a method 350 of implantation of e.g., a non-sensor apparatus, such as a therapy apparatus or implant, is disclosed. At step 352, the patient (e.g., human being) is evaluated for: (i) the propriety of use of the implantable apparatus; (ii) the best or desired implantation site (which, as discussed elsewhere herein, may or may not be a previously utilized site); and (iii) any other factors which the heath care provider should consider, such as recent other surgeries, recent ingestion of pharmacological agents, and the like.

At step 354, the patient is prepared for surgery (whether traditional, laparoscopic, or otherwise), as discussed previously herein. The incision site(s) may also be marked on the patient at this point.

At step 356, the sensor is prepared for surgical implantation in the patient. In one embodiment, the exemplary therapy apparatus or implant is (i) removed from its packing/shipping container, preserving its sterility after removal and before implantation, (ii) powered up (if applicable), and (iii) functionally tested so as to assure its operability in certain regards, as applicable.

At step 358 of the method 350, the patient is surgically incised at the target location, and a cavity formed below the skin and extending to the fascia underlying the target location. In one variant, the user's superficial (scarpal) fascia is incised, and the adipose tissue 405 immediately proximate the deeper fascial membrane 402 (i.e., anterior abdominal fascia; see FIGS. 4 and 5) is merely separated from the fascial membrane so as to form the desired cavity or pocket 502, with little or no tissue removal from the patient. In an alternate variant, the surgeon may remove a small amount of fat cells or tissue in the region in order to accommodate the volume of the therapy apparatus or implant. In yet another variant, a specialized "pocket forming" surgical tool may be inserted into the location where the pocket is desired, and then removed to create a suitable pocket.

As noted supra, the target implantation site is in one implementation chosen to be in the patient's lower abdomen, lateral to the midline, inferior to the umbilicus and superior to the inguinal ligament. While other sites may be used consistent with the present disclosure, this site often has significant advantages associated therewith, both for the implanting surgeon and the patient; e.g., less damage to the patient's tissue and blood vessels occurs when performing implantation in this region.

Once the cavity or pocket 502 (FIG. 5) is formed, the therapy apparatus or implant is implanted within the cavity/pocket per step 360.

Per step 362 of the method 350, the therapy apparatus or implant can optionally be affixed or "anchored" to the patient's anatomy so as to, inter alia, preclude the apparatus or implant from moving or dislocating within the patient after implantation (and potentially affecting the operation thereof).

Lastly, per step 364 of the method 350, the surgical incision (and optionally the cavity itself) are closed, and post-surgical treatment is applied to the patient.

"Re-Use" of Surgical Sites

The present disclosure further contemplates that (i) the same implantation site and/or incision used for sensor implantation can be used for successive implantations of sensors and/or other apparatus, (ii) a different implantation site and/or incision can be used for such successive implantations (e.g., access to the same fascial-proximate region may occur via the same or different incision, and access to a different fascial-proximate region may occur via the same or different incision), and (iii) a pre-existing or prior incision from an unrelated procedure (e.g., appendectomy, cesarean section, etc.) may be "repurposed" for implantation, thereby mitigating aesthetic concerns relating to the creation of new scars. Hence, a healthcare provider is advantageously given a range of options dependent upon the application; e.g., particular patient desires, complications, changes since the last implantation, etc.

Figure 6:
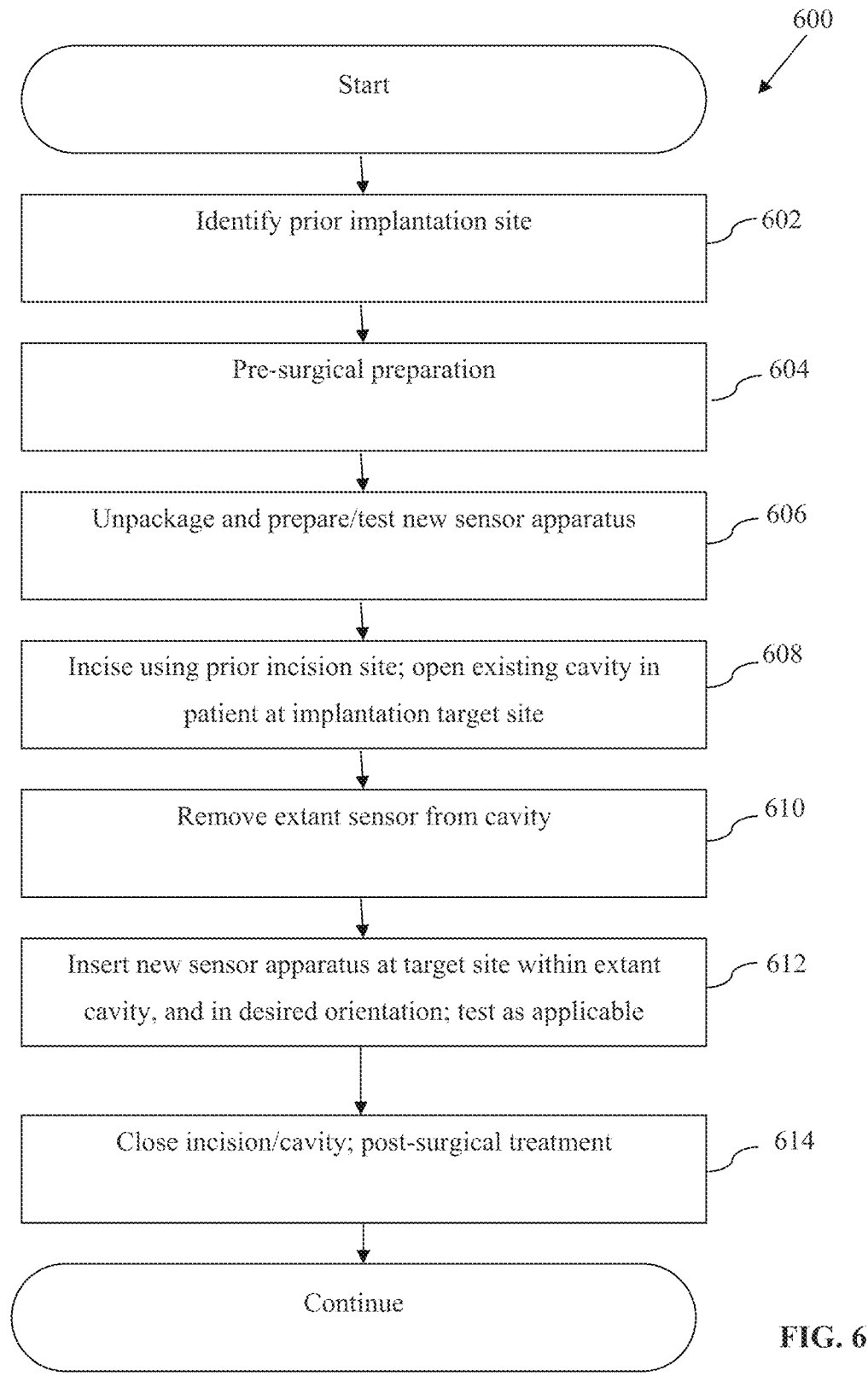
FIG. 6 is a generalized logical flow diagram illustrating an exemplary embodiment of a method of surgical implantation utilizing a common implantation site and incision, in accordance with the present disclosure.

As shown in FIG. 6, the foregoing "re-use" methodology for implantation 600 first identifies the site of the prior implantation and incision at step 602. At step 604, the patient is prepared for surgery. As noted above, such surgery (and preparation) is advantageously minimal, typically on an outpatient basis with local anesthetic.

At step 606, the new sensor to be implanted is unpackaged and readied for implantation, as described supra. At step 608, the prior incision is re-incised (either wholly or in part), and the extant cavity formed within the tissue re-opened such that the implanted sensor apparatus can be removed (step 610).

Per step 612, the "new" sensor apparatus 200 is disposed within the cavity and tested as appropriate, in the desired position and orientation as previously described. Note that depending on the degree of FBR encountered (e.g., contouring of the tissue proximate the sensor elements 206, etc.), it may be desirable to locate the sensing region 204 in a slightly different location, such as in areas where no contouring or "imprint" has occurred. Conversely, there are situations where it may be desirable to utilize the already contoured portion of the tissue (i.e., mimic placement of the prior sensor apparatus as closely as possible).

Finally, per step 614, the incision (and optionally the cavity itself as desired) is closed (e.g., sutured or adhered using e.g., an adhesive bandage, surgical staples, or tissue adhesive), with the patient receiving post-surgery treatment and processing for discharge as required.

It will be recognized that the term "new sensor apparatus" in the preceding discussion is not limited to a distinct physical device. For example, the procedure of FIG. 6 may be modified such that the existing (implanted) device is merely provisioned for use again within the same patient (e.g., by changing out the battery, other renewable component, or the like). It is recognized that to the degree that a patient's body has already "assimilated" the sensor in terms of FBR or other biological processes, there may be advantages to re-use of the sensor apparatus (or parts thereof) in that same patient in terms of, e.g., reduction of tissue trauma in explantation (such as where the exemplary battery or the like can be replaced without a full explant of the sensor apparatus), or where reduced levels of FBR are anticipated by leaving the already implanted device in vivo. These considerations should be weighed, however, against other factors such as degradation or loss of one or more sensor element pairs due to e.g., FBR occurring prior to the explant procedure.

Anecdotal Performance

Human clinical trials conducted by the Assignee hereof authorized by the U.S. Food and Drug Association (FDA) to date indicate superior performance of the foregoing techniques and apparatus, including notably (i) the ability of the sensor apparatus to remain implanted for extended periods without deleterious foreign body response to the sensor from the host which impairs the operation of the sensor, (ii) general insensitivity to ingested or locally injected substances which might otherwise interfere with the performance of the device (e.g., acetaminophen, insulin injections, etc.) and (iii) the ability of the sensor apparatus to provide a stable output for extended (e.g., multiple week) intervals. These advantages are due at least in part by virtue of the selected target location being deep(er) within the abdominal subcutaneous tissue of the patient (e.g., proximate the fascia), and the orientation of the sensing region of the apparatus 200 away from possible sources of interference or degradation.

Figure 7:
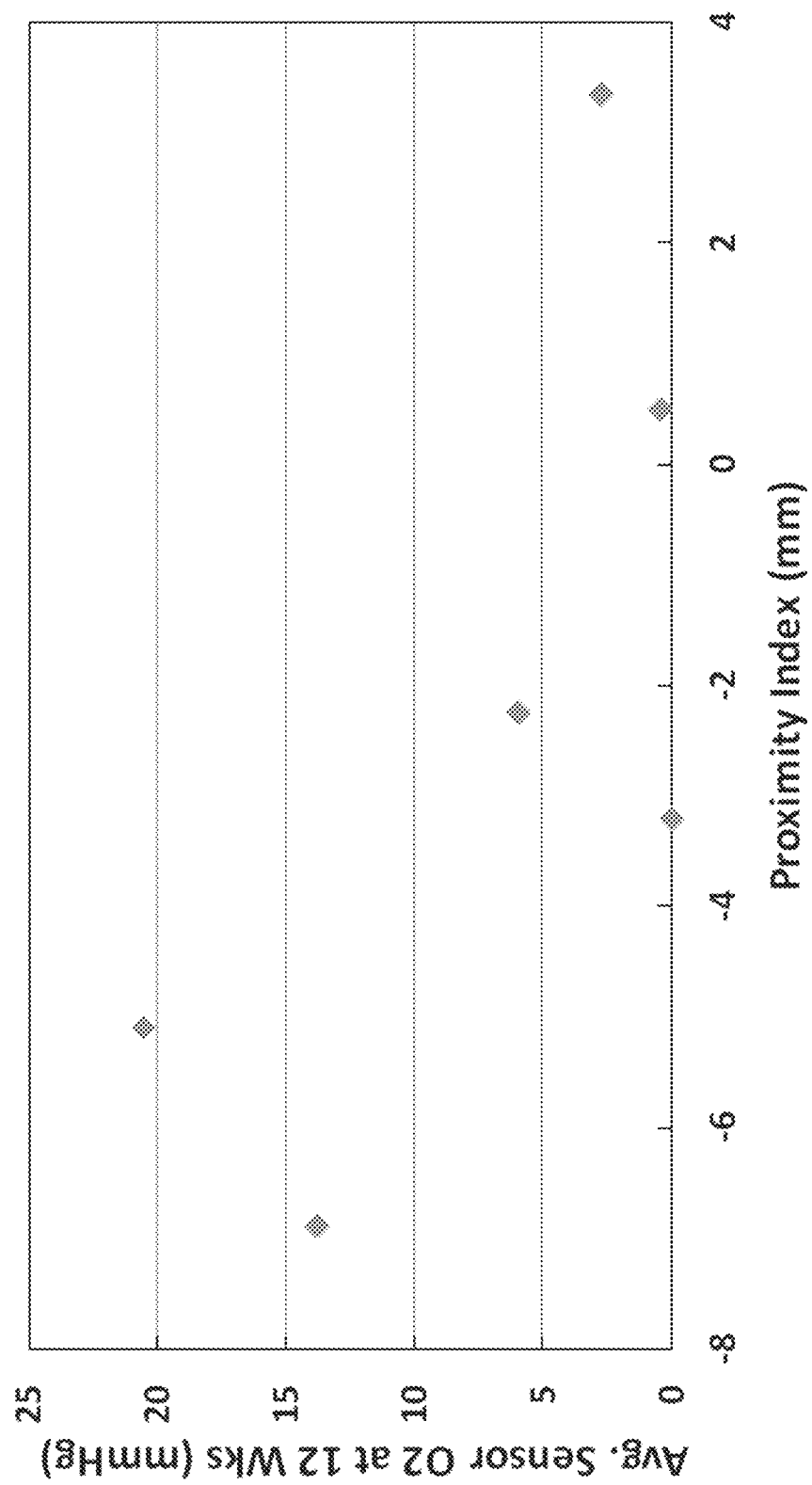
FIG. 7 herein is a plot of "proximity index" vs. average sensor $O_2$ level at 12 weeks (implanted duration) obtained during clinical trials by the Assignee hereof using an exemplary sensor device.

FIG. 7 herein is a plot of "proximity index" vs. average sensor $O_2$ level at 12 weeks (implanted duration), which illustrates exemplary anecdotal data obtained by the Assignee hereof during trials of a generally comparable sensing device and using, inter alfa, ultrasound techniques. Specifically, the data of FIG. 7 demonstrates the aforementioned stability of output for extended periods, which is in part afforded by the sensor device's access to the blood supply by virtue of its "deep" placement. Each point on the graph of FIG. 7 represents the average of the output from the four (4) oxygen reference electrodes on a given implanted device. The "proximity index" metric of FIG. 7 provides an indication of the distance between the sensing area aspect of the implanted device and the underlying muscle layer. Any positive value of the index indicates physical separation (i.e., lack of intimate contact between the sensing area and the target tissue such as the muscle fascia). Conversely, any negative index value indicates close contact between the sensing area and the muscle fascia. Hence, as can be seen in FIG. 7, excellent physical contact of the sensing area of the device and the muscle fascia was maintained.

It will be recognized that while certain embodiments of the present disclosure are described in terms of a specific sequence of steps of a method, these descriptions are only illustrative of the broader methods described herein, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure and claimed herein.

While the above detailed description has shown, described, and pointed out novel features as applied to various embodiments, it will be understood that various omissions, substitutions, and changes in the form and details of the device or process illustrated may be made by those skilled in the art without departing from principles described herein. The foregoing description is of the best mode presently contemplated. This description is in no way meant to be limiting, but rather should be taken as illustrative of the general principles described herein. The scope of the disclosure should be determined with reference to the claims.

What is claimed is:

1. A method of implanting a sensor in a living entity, the sensor configured for monitoring of at least one physiological parameter, the method comprising:
   perforating an outer layer of tissue of the living entity so as to gain access to tissue below;
   forming a cavity within a portion of the accessed tissue;
   disposing the sensor at least partly within the cavity so that the sensor is situated in a desired position relative to at least one anatomical feature of the living entity, the sensor comprising at least one non-peroxide, oxygen-based glucose sensing element disposed in a first sensing region thereof;
   closing off the perforation such that the implanted sensor is substantially contained and operable within the living entity;
   operating the implanted sensor for a period of time to monitor the at least one physiological parameter;
   minimizing a tissue response effect of the implanted sensor on the accessed tissue, thereby limiting a foreign body response of the accessed tissue and allowing the accessed tissue contour around the sensor and form a contoured site, the minimizing the tissue response effect at least in part comprising limiting exposure of the tissue to any significant concentration of peroxides via utilizing the at least one non-peroxide, oxygen-based glucose sensing element for the operating of the implanted sensor for the period of time to monitor the at least one physiological parameter, the contoured site comprising a shape corresponding to one or more surface features of the sensing region; and
   after the period of time, explanting the sensor while substantially maintaining the shape of the contoured site corresponding to the one or more surface features of the first sensing region, and implanting a new sensor such that a second sensing region thereof is positioned into the shape corresponding to the one or more surface features of the first sensing region at the contoured site.

2. The method of claim 1, wherein the sensor comprises a substantially continuous glucose sensor, and the at least one non-peroxide, oxygen-based glucose sensing element comprises a plurality of individual non-peroxide, oxygen-based glucose sensing elements disposed in the first sensing region; and
   wherein the method further comprises disposing the sensor within the cavity so that it is both (i) situated in the desired position relative to the at least one anatomical feature, and (ii) oriented with the sensing region thereof substantially facing away from an epidermal layer of the living entity overlying the portion of the accessed tissue.

3. The method of claim 1, wherein:
   the forming the cavity comprises forming the cavity so that at least a portion thereof is immediately proximate a fascia of the living entity; and
   the desired position relative to at least one anatomical feature comprises the first sensing region being disposed within the at least portion of the cavity such that the first sensing region is immediately proximate the fascia and in contact with tissue proximate thereto.

4. The method of claim 1, wherein the perforating the outer layer of tissue of the living entity comprises forming an incision on a lower abdomen of the living entity, the formed incision disposed lateral to a midline of the living entity, and inferior to an umbilicus and superior to an inguinal ligament of the living entity.

5. The method of claim 4, wherein the forming the cavity comprises separating at least a first layer of subcutaneous tissue proximate to a superficial fascial layer from a second layer of subcutaneous tissue without any significant cutting or removal of tissue, the cavity formed such that a longitudinal axis of the cavity is substantially parallel to the midline and extends substantially superior from the incision.

6. The method of claim 5, wherein the first layer of subcutaneous tissue comprises adipose tissue, and the second layer of subcutaneous tissue comprises at least one of muscular fascia tissue or muscular tissue.

7. The method of claim 1, wherein the minimizing the tissue response effect of the implanted sensor on the accessed tissue at least in part comprises implanting the sensor beneath an adipose tissue layer of the living subject.

8. The method of claim 1, wherein:
   the sensor comprises an oxygen-based glucose sensor; and
   the minimizing the tissue response effect of the implanted sensor on the accessed tissue at least in part comprises enabling long-term implantation of the oxygen-based glucose sensor via a face of the sensor contacting oxygen-rich tissue below an adipose tissue layer of the living entity.

9. The method of claim 1, wherein the implanting the new sensor such that the second sensing region thereof is positioned at the contoured site at least in part comprises enhancing mechanical coupling between the new sensor and the accessed tissues, thereby minimizing a subsequent tissue response effect of the new implanted sensor on the accessed tissue.

10. A method of providing treatment to a living being, the method comprising:
   forming an incision in a portion of an abdomen of the living being;
   forming a cavity within a portion of the solid tissue of the living being accessible via the incision;
   disposing a first sensor apparatus at least partly within the cavity so that the first sensor apparatus is situated in a desired position and orientation relative to at least one anatomical feature of the living being;
   closing off at least a portion of the formed incision such that the first sensor apparatus is substantially contained and operable within the living being;
   utilizing the first sensor apparatus to monitor at least one physiological parameter associated with the living being for a first period of time and enabling the tissue to form a contoured portion around one or more first external features of the first sensor apparatus during the first period of time;

minimizing a tissue response effect of the first sensor apparatus on the accessed tissue, thereby limiting a foreign body response of the accessed tissue;

subsequently re-incising the portion of the abdomen and explanting the first sensor apparatus from the living being while maintaining the contoured portion of the tissue, the explanting of the first sensor apparatus from the living being while maintaining the contoured portion of the tissue enabled at least in part by the minimizing of the tissue response effect;

disposing a second sensor apparatus at least partly within the cavity within which the first sensor apparatus was previously disposed so that the second sensor apparatus is situated in the desired position and orientation relative to the at least one anatomical feature of the living being, the disposing of the second sensor apparatus comprising:

identifying the contoured portion of the tissue within the cavity; and positioning each of one or more second external features of the second sensor apparatus into a corresponding shape within the contoured portion of the tissue;

closing off the re-incised portion so that the second sensor apparatus is substantially contained and operable within the living being; and utilizing the second sensor apparatus to monitor the at least one physiological parameter associated with the living being for a second period of time.

11. The method of claim 10, wherein the subsequently re-incising comprises substantially utilizing the incision.

12. The method of claim 11, wherein the subsequently re-incising, and the disposing the second sensor apparatus within the cavity within which the first sensor apparatus was previously disposed, cooperate to reduce the propensity for thickening of the fibrous encapsulation of the second sensor apparatus by the living being as part of the method.

13. The method of claim 10, wherein the subsequently re-incising is performed before expiry of the first period of time such that said monitoring of the at least one physiological parameter associated with the living being continues substantially uninterrupted.

14. The method of claim 13, wherein the utilizing the second sensor apparatus to monitor the at least one physiological parameter associated with the living being for a second period of time comprises commencing the second period of time before said closing off of the cavity after the disposing of the second sensor apparatus at least partly within the cavity.

15. The method of claim 10, wherein the forming the incision in the portion of the abdomen comprises forming an incision on a lower abdomen of the living being, the formed incision disposed lateral to a midline of the living being, and inferior to an umbilicus and superior to an inguinal ligament of the living being.

16. The method of claim 15, wherein the forming the cavity comprises separating at least a first layer of subcutaneous tissue proximate to a superficial fascial layer from a second layer of subcutaneous tissue without any significant cutting or removal of tissue, the cavity formed such that a longitudinal axis of the cavity is substantially parallel to the midline.

17. The method of claim 16, wherein the first layer of subcutaneous tissue comprises adipose tissue, and the second layer of subcutaneous tissue comprises at least one of muscular fascia tissue or muscular tissue.

18. The method of claim 10, wherein the minimizing of the tissue response effect at least in part comprises utilizing one or more oxygen-based sensing elements for the monitoring of the at least one physiological parameter, and thereby limiting exposure of the tissue to peroxide byproducts during the monitoring.

19. A method of implanting a replacement blood analyte sensor in a living entity, the method comprising:

forming an incision in a portion of an abdomen of the living entity so as to gain access to a cavity in tissue below, the cavity disposed between a layer of adipose tissue proximate to a superficial fascial layer and a muscular fascia layer, the cavity having at least one blood analyte sensor disposed therein, the at least one blood analyte sensor having been operated within the living entity for a first period of time to monitor signals related to at least one blood analyte;

removing the at least one blood analyte sensor from the cavity;

disposing the replacement blood analyte sensor at least partly within the cavity within which the at least one blood analyte sensor was previously disposed;

closing off the incision such that the replacement sensor blood analyte sensor is substantially contained and operable within the living entity; and operating the replacement blood analyte sensor within the living entity for a second period of time to monitor subsequent signals related to the at least one blood analyte;

wherein the disposing the replacement blood analyte sensor at least partly within the cavity at least in part comprises:

identifying a contoured portion of the tissue in the muscular fascia layer which has contoured to at least a shape of a first sensing region of the at least one blood analyte sensor without encouraged foreign body response; and positioning each of one or more external features of a second sensing region of the replacement blood analyte sensor into a corresponding shape within the contoured portion of the tissue in the muscular fascia layer.

20. The method of claim 19, wherein the positioning each of the one or more external features of the second sensing region of the replacement blood analyte sensor into the corresponding shape within the contoured portion of the tissue enhances mechanical coupling of the replacement blood analyte sensor with the tissue of the living entity.

21. The method of claim 19, wherein the forming the incision in the portion of the abdomen comprises forming an incision on a lower abdomen of the living entity, the formed incision disposed lateral to a midline of the living entity, and inferior to an umbilicus and superior to an inguinal ligament of the living entity.

22. The method of claim 19, wherein the disposing the replacement blood analyte sensor at least partly within the cavity is performed before expiry of the first period of time such that monitoring of the at least one blood analyte within the living entity continues substantially uninterrupted.

23. The method of claim 19, wherein disposing the replacement blood analyte sensor at least partly within the cavity at least in part comprises positioning the replacement blood analyte sensor such that the second sensing region thereof is oriented toward the muscular fascia layer.

24. The method of claim 19, wherein the disposing the replacement blood analyte sensor at least partly within the cavity, within which the at least one blood analyte sensor was previously disposed, reduces a propensity for thickening of fibrous encapsulation of the replacement blood analyte sensor apparatus by the living entity.

25. The method of claim 19, wherein the disposing the replacement blood analyte sensor at least partly within the cavity, within which the at least one blood analyte sensor was previously disposed, reduces foreign body response to the replacement blood analyte sensor by the living entity.

* * * * *